US012575875B2

(12) United States Patent
Hsu et al.

(10) Patent No.: US 12,575,875 B2
(45) Date of Patent: Mar. 17, 2026

(54) SURGICAL DEVICE AND METHODS

(71) Applicant: Aulea Medical, Inc., San Ramon, CA (US)

(72) Inventors: George Chao-chih Hsu, San Ramon, CA (US); Steve Duddy, San Mateo, CA (US); George Surjan, Los Gatos, CA (US)

(73) Assignee: Aulea Medical, Inc., San Ramon, CA (US)

( * ) Notice: Subject to any disclaimer, the term of this patent is extended or adjusted under 35 U.S.C. 154(b) by 530 days.

(21) Appl. No.: 18/063,685

(22) Filed: Dec. 9, 2022

(65) Prior Publication Data

US 2023/0190361 A1     Jun. 22, 2023

Related U.S. Application Data

(60) Provisional application No. 63/290,915, filed on Dec. 17, 2021.

(51) Int. Cl.
   *A61B 18/14*        (2006.01)
   *A61B 18/00*        (2006.01)
(52) U.S. Cl.
   CPC   *A61B 18/1445* (2013.01); *A61B 2018/00577* (2013.01); *A61B 2218/002* (2013.01)
(58) Field of Classification Search
   CPC ...... A61B 18/1445; A61B 2018/00577; A61B 2218/002
   USPC ......................................................... 604/319
   See application file for complete search history.

(56) References Cited

U.S. PATENT DOCUMENTS

| | | | | |
|---|---|---|---|---|
| 3,833,000 | A | * | 9/1974 | Bridgman ............. A61M 1/732 604/319 |
| 4,376,053 | A | * | 3/1983 | Bullock ................ A01J 5/0134 D23/209 |
| 4,607,621 | A | | 8/1986 | Wheeler |
| 4,643,197 | A | * | 2/1987 | Greene ................... A61M 1/79 604/319 |
| 4,974,075 | A | | 11/1990 | Nakajima |
| 4,989,586 | A | | 2/1991 | Furukawa |
| 5,197,971 | A | | 3/1993 | Bonutti |
| 5,250,047 | A | | 10/1993 | Rydell |

(Continued)

FOREIGN PATENT DOCUMENTS

| | | | | |
|---|---|---|---|---|
| WO | WO-9717028 A1 | * | 5/1997 | ......... A61B 18/1206 |
| WO | 2016175980 A1 | | 11/2016 | |

(Continued)

OTHER PUBLICATIONS

"Examination Report for EP19748025.4, mailed on Jul. 23, 2023 ppg. all".

(Continued)

*Primary Examiner* — Andrew J Mensh
(74) *Attorney, Agent, or Firm* — Dorsey & Whitney LLP

(57) ABSTRACT

Apparatus for performing electrosurgical tissue resections, such as transurethral resection of the include motor-driven cutters which drive both a shaft of the cutter and a cutter electrode, either or selectively. The systems often include controllers which coordinate movements of the shaft, electrodes, and other external components. The apparatus may include integrated imaging and light illumination systems. The apparatus may include integrated tissue filter and collection traps.

11 Claims, 24 Drawing Sheets

(56) References Cited

U.S. PATENT DOCUMENTS

| | | | |
|---|---|---|---|
| 5,256,160 A * | 10/1993 | Clement | B01J 37/10 |
| | | | 604/319 |
| 5,354,302 A | 10/1994 | Ko | |
| 5,752,970 A | 5/1998 | Yoon | |
| 5,824,002 A | 10/1998 | Gentelia et al. | |
| 5,906,615 A | 5/1999 | Thompson | |
| 6,358,238 B1 | 3/2002 | Sherry | |
| 6,508,825 B1 | 1/2003 | Selmon et al. | |
| 6,537,288 B2 | 3/2003 | Vargas et al. | |
| 6,770,026 B2 | 8/2004 | Kan et al. | |
| 6,939,318 B2 | 9/2005 | Stenzel | |
| 7,056,329 B2 | 6/2006 | Kerr | |
| 7,604,648 B2 | 10/2009 | Kerr | |
| 7,744,595 B2 | 6/2010 | Truckai et al. | |
| 8,221,404 B2 | 7/2012 | Truckai | |
| 8,262,619 B2 | 9/2012 | Chebator et al. | |
| 8,337,394 B2 | 12/2012 | Vakharia | |
| 8,622,894 B2 | 1/2014 | Banik et al. | |
| 9,056,182 B2 | 6/2015 | Moulton et al. | |
| 9,308,077 B2 | 4/2016 | Behan et al. | |
| 9,839,473 B2 | 12/2017 | Germain et al. | |
| 9,848,947 B2 | 12/2017 | Sukthankar et al. | |
| 9,980,715 B2 | 5/2018 | Marino et al. | |
| 10,004,556 B2 | 6/2018 | Orczy-Timko et al. | |
| 10,383,682 B2 | 8/2019 | Sartor et al. | |
| 10,675,087 B2 | 6/2020 | Truckai et al. | |
| 10,736,491 B2 | 8/2020 | Truckai | |
| 10,758,301 B2 | 9/2020 | Ciccone et al. | |
| 10,869,716 B2 | 12/2020 | Sartor et al. | |
| 10,939,933 B2 | 3/2021 | Truckai | |
| 11,141,045 B2 | 10/2021 | Kucharski et al. | |
| 11,246,649 B2 | 2/2022 | Germain et al. | |
| 11,246,650 B2 | 2/2022 | Germain et al. | |
| 11,272,835 B2 | 3/2022 | Hsu et al. | |
| 11,304,747 B2 | 4/2022 | Simani et al. | |
| 11,446,080 B2 | 9/2022 | Hsu et al. | |
| 11,497,551 B2 | 11/2022 | Germain et al. | |
| 11,648,048 B1 | 5/2023 | Barry et al. | |
| 11,672,593 B2 | 6/2023 | Germain et al. | |
| 11,707,182 B2 | 7/2023 | Weeks et al. | |
| 11,717,342 B2 | 8/2023 | Willhite et al. | |
| 11,723,681 B2 | 8/2023 | Germain et al. | |
| 11,826,023 B2 | 11/2023 | Craig et al. | |
| 11,883,053 B2 | 1/2024 | Germain et al. | |
| 11,944,276 B2 | 4/2024 | Hsu et al. | |
| 12,207,864 B2 | 1/2025 | Hsu et al. | |
| 12,336,751 B2 | 6/2025 | Hsu et al. | |
| 2002/0042622 A1 | 4/2002 | Vargas et al. | |
| 2002/0111564 A1 | 8/2002 | Burbank et al. | |
| 2003/0181905 A1 | 9/2003 | Long | |
| 2004/0073088 A1 | 4/2004 | Friedman et al. | |
| 2004/0073195 A1 | 4/2004 | Cucin | |
| 2004/0082969 A1 | 4/2004 | Kerr | |
| 2004/0138655 A1 | 7/2004 | McClurken et al. | |
| 2005/0010203 A1 | 1/2005 | Edwards et al. | |
| 2005/0070889 A1 | 3/2005 | Nobis et al. | |
| 2005/0234294 A1 | 10/2005 | Saadat et al. | |
| 2005/0272975 A1 | 12/2005 | McWeeney et al. | |
| 2007/0021616 A1 | 1/2007 | Martin et al. | |
| 2007/0051375 A1 | 3/2007 | Milliman | |
| 2007/0135778 A1 * | 6/2007 | Murray | A61M 1/631 |
| | | | 604/319 |
| 2007/0213704 A1 | 9/2007 | Truckai et al. | |
| 2007/0244440 A1 | 10/2007 | Pal et al. | |
| 2008/0097476 A1 | 4/2008 | Peh et al. | |
| 2008/0161902 A1 | 7/2008 | Poulsen | |
| 2008/0249553 A1 | 10/2008 | Gruber et al. | |
| 2009/0018603 A1 | 1/2009 | Mitelberg et al. | |
| 2009/0076329 A1 | 3/2009 | Su et al. | |
| 2009/0270849 A1 | 10/2009 | Truckai et al. | |
| 2010/0081877 A1 | 4/2010 | Vakharia | |
| 2010/0249602 A1 | 9/2010 | Buckley et al. | |
| 2010/0305565 A1 | 12/2010 | Truckai et al. | |
| 2011/0028898 A1 | 2/2011 | Clark et al. | |
| 2011/0160539 A1 | 6/2011 | Robertson | |
| 2012/0083740 A1 | 4/2012 | Chebator et al. | |
| 2012/0323180 A1 | 12/2012 | Chebator et al. | |
| 2012/0330292 A1 | 12/2012 | Shadduck et al. | |
| 2013/0046304 A1 | 2/2013 | Germain et al. | |
| 2013/0090642 A1 | 4/2013 | Shadduck et al. | |
| 2013/0172870 A1 | 7/2013 | Germain et al. | |
| 2013/0231652 A1 | 9/2013 | Germain et al. | |
| 2014/0200398 A1 | 7/2014 | Hawkins et al. | |
| 2014/0236088 A1 | 8/2014 | Al-Rashdan et al. | |
| 2014/0236122 A1 | 8/2014 | Anderson et al. | |
| 2014/0257269 A1 | 9/2014 | Woloszko et al. | |
| 2014/0276908 A1 | 9/2014 | Raybin et al. | |
| 2014/0303611 A1 | 10/2014 | Shadduck et al. | |
| 2014/0324065 A1 | 10/2014 | Bek et al. | |
| 2014/0336643 A1 | 11/2014 | Orczy-Timko et al. | |
| 2015/0105791 A1 | 4/2015 | Truckai | |
| 2015/0157387 A1 | 6/2015 | Ouyang et al. | |
| 2015/0157396 A1 | 6/2015 | Germain et al. | |
| 2015/0230697 A1 | 8/2015 | Phee et al. | |
| 2015/0250992 A1 | 9/2015 | Morriss et al. | |
| 2016/0089184 A1 | 3/2016 | Truckai et al. | |
| 2016/0095615 A1 | 4/2016 | Orczy-Timko et al. | |
| 2016/0106562 A1 | 4/2016 | Puckett et al. | |
| 2016/0228116 A1 | 8/2016 | Milliman | |
| 2016/0235279 A1 | 8/2016 | Yamakawa | |
| 2016/0346037 A1 | 12/2016 | Truckai et al. | |
| 2017/0014252 A1 | 1/2017 | Kelly | |
| 2017/0035274 A1 | 2/2017 | Mikkaichi | |
| 2017/0086918 A1 | 3/2017 | Shadduck et al. | |
| 2017/0105507 A1 | 4/2017 | Golding | |
| 2017/0105607 A1 | 4/2017 | Truckai | |
| 2017/0105748 A1 | 4/2017 | Truckai | |
| 2017/0181793 A1 | 6/2017 | Germain et al. | |
| 2017/0258519 A1 | 9/2017 | Germain et al. | |
| 2017/0265892 A1 | 9/2017 | Winegar et al. | |
| 2017/0333119 A1 | 11/2017 | Truckai | |
| 2017/0333120 A1 | 11/2017 | Truckai | |
| 2018/0036156 A1 | 2/2018 | Kelly | |
| 2018/0071015 A1 | 3/2018 | Germain et al. | |
| 2018/0221054 A1 | 8/2018 | Truckai | |
| 2018/0280077 A1 | 10/2018 | Orczy-Timko et al. | |
| 2019/0133676 A1 | 5/2019 | Hsu et al. | |
| 2019/0201023 A1 | 7/2019 | Shelton et al. | |
| 2019/0231416 A1 | 8/2019 | Hsu et al. | |
| 2021/0059748 A1 | 3/2021 | Hsu et al. | |
| 2022/0322926 A1 | 10/2022 | Hsu et al. | |
| 2023/0181239 A1 | 6/2023 | Hsu et al. | |
| 2024/0206957 A1 | 6/2024 | Hsu et al. | |
| 2024/0341585 A1 | 10/2024 | Hsu et al. | |

FOREIGN PATENT DOCUMENTS

| | | |
|---|---|---|
| WO | 2016204997 A1 | 12/2016 |
| WO | 2019094643 A1 | 5/2019 |
| WO | 2019152377 A1 | 8/2019 |
| WO | 2022031851 A2 | 2/2022 |

OTHER PUBLICATIONS

International Search Report and Written Opinion for PCT/US2018/059897, mailed on Jan. 17, 2019.

International Search Report and Written Opinion for PCT/US2021/044545, mailed on Feb. 1, 2022.

"Extended European Search Report for EP19748025.4, mailed on Sep. 17, 2021".

"International Search Report and Written Opinion for PCT/US2019/015585, mailed on Apr. 26, 2019".

U.S. Appl. No. 19/037,861, titled "Surgical Device and Methods" filed Jan. 27, 2025, pp. all pages of application as filed.

U.S. Appl. No. 18/615,481, titled "Surgical Device and Methods" filed Mar. 25, 2024, pp. all pages of application as filed.

Extended European Search Report for EP Appl. No. 24151142.7, mailed on Feb. 20, 2024.

U.S. Appl. No. 18/594,942, titled "Surgical Device and Methods" filed Mar. 4, 2024, pp. all pages of application as filed.

Extended European Search Report for European Patent Application No. EP21853253.9, mailed Jul. 22, 2024, pp. all.

(56) References Cited

OTHER PUBLICATIONS

Anonymous, "Coaxial cable", Wikipedia, Jul. 28, 2020, XP093183155, retried from the Internet: URL: https://en.wikipedia.org/w/index/php?title=coaxial_cable&oldid=969906879.

* cited by examiner

LED SOURCE 160

IMAGE PROCESSOR 140

RF SOURCE 155A

MOTOR ELEC SOURCE 155B

CONTROLLER 150

115

120

SURGICAL DEVICE AND METHODS

CROSS-REFERENCE TO RELATED APPLICATION

This application claims the benefit of U.S. Provisional Application No. 63/290,915, filed on Dec. 17, 2021, the full disclosure of which is incorporated herein by reference.

BACKGROUND OF THE INVENTION

1. Field of the Invention

The present invention relates to devices and methods for resecting and removing tissue from an interior of a patient's body, for example in a transurethral resection of bladder tumor or the resection of prostate tissue to treat benign prostatic hyperplasia.

Electrosurgical cutting devices often comprise a shaft or sleeve having a tissue extraction lumen with one or more radio frequency (RF) cutting blades arranged to resect tissue which may then be drawn into the extraction lumen, often via vacuum assistance through a cutting window. Most such electrosurgical tissue cutting devices rely on manually engaging the cutting window against the target tissue to be resected. While such manual engagement is often sufficient, in other cases, such as in laparoscopic procedures having limited access and field of view, the target tissue can be difficult to visualize prior to resection and, in particular, it can be difficult to assure that the optimum target site has been engaged by the cutting window. For these reasons, it would be desirable to provide improved electrosurgical cutting tools having improved visibility and ability engage and immobilize tissue prior to cutting and to extract the tissue from tools after cutting.

For resection of remote tissue sites, such as the bladder or prostate, it is usually desirable to introduce the surgical cutter through a tubular introducer device. Though such tubular introducers can be advanced "blind," i.e., without direct optical visualization, it is frequently advantageous to provide such introducers with direct visualization. For example, it would be desirable to use an endoscope to observe the urethra while transurethrally advancing an introducer sheath for subsequent resection of a bladder tumor (e.g., by transurethral resection of the bladder tumor, commonly referred to as TURBT) or prostrate tissue (transurethral resection of the prostate, commonly referred to as TURP). Once the introducer sheath is in place and the surgical cutter has been introduced, however, it will still be necessary to move a cutter element on the surgical cutter to resect the tissue. Heretofore, this has typically been accomplished by manually reciprocating a cutter assembly on the tissue resecting apparatus. Manual resection, while generally effective, can be difficult to control and, in particular, can be difficult to coordinate with other aspects of the resection procedure, such as applying RF power, applying a vacuum to aspirate tissue fragments and debris, and the like.

For these reasons, it would be desirable to provide improved apparatus, systems and methods for resecting tissue in TURBT, prostatectomies, and other procedures. It would be particularly desirable to provide apparatus, systems and methods which provide improved control of tissue resection including but not limited to enhanced coordination of cutter movement control, cutting power control, vacuum aspiration control, and the like. At least some of these objectives will be met by the inventions described below.

2. Listing of Background Art

Related patents and published applications include U.S. Pat. Nos. 8,221,404; 7,744,595; U.S. Pat. Publ. 2014/0336643; U.S. Pat. Publ. 2010/0305565; U.S. Pat. Publ. 2007/0213704; U.S. Pat. Publ. 2009/0270849; U.S. Pat. Publ. 2013/0090642; U.S. Pat. Publ. 2013/0046304; U.S. Pat. Publ. 2013/0172870; U.S. Pat. Publ. 2015/0105791; U.S. Pat. Publ. 2015/0157396; U.S. Pat. Publ. 2016/0089184; U.S. Pat. Publ. 2016/0095615; U.S. Pat. Publ. 2017/0086918; U.S. Pat. Publ. 2017/0181793; and U.S. Pat. Publ. 2018/0071015. See also commonly assigned, published applications: U.S. Pat. Publ. 2014/0336643; U.S. Pat. Publ. 2017/0105748; U.S. Pat. Publ. 2017/0105607; U.S. Pat. Publ. 2017/0333120; U.S. Pat. Publ. 2017/0333119; U.S. Pat. Publ. 2018/0221054; and U.S. Pat. Publ. 2018/0280077.

SUMMARY OF THE INVENTION

The present invention provides apparatus, systems, and methods for performing electrosurgical resections in minimally invasive procedures. While the apparatus, systems, and methods are particularly suitable for performing transurethral resection of a bladder tumor (TURBT) or of prostate tissue (TURP), they will also find use in a variety of other laparoscopic and other endoscopic and endosurgical procedures. In some embodiments, the apparatus comprises motor-driven cutters, where the motors are configured to drive both a shaft of the cutter and a cutter electrode, either independently, contemporaneously, or selectively independently and contemporaneously. In some embodiments, systems comprise the cutters together with a digital or other controller configured to coordinate movements of the shaft, electrodes, and other external components such as a radiofrequency power supply (e.g. by selecting a cutting or a coagulation waveform, power, timing, etc.), a negative pressure source, and the like. In some instances, the motor-driven loops and other tissue resection devices may be combined with light-emitting diodes (LED's) and other illumination sources. In particular instances, the motor-driven loops and other tissue resection devices may be combined with two or more light sources having different wavelengths, for example white and blue light-emitting diodes (LED's) and other illumination sources which enhanced blue light cystoscopy and other visualization techniques. In still other embodiments, tissue resection devices may be combined with tissue collection devises such a filters and traps, which facilitate collection of tissue particles during a procedure to permit rapid histological and other testing to detect malignancies and other tissue abnormalities. The present invention further provides methods for using the apparatus and systems as just described for bladder tumor resections, prostatectomies and other tissue resection procedures.

In a first aspect, the present invention provides a tissue "trap" for use with a tissue removal device having a fluid outflow connector configured to direct waste fluid to a waste fluid collection reservoir. The tissue trap comprises a collector housing having (a) a fluid inflow port configured to receive waste fluid from the fluid outflow connector of the tissue removal device and (b) a fluid outflow port configured to direct filtered waste fluid to the fluid collection reservoir. A collector vial has an inlet end, and outlet end, and a filter member therebetween, where the filter member is configured to trap tissue particles released into the waste fluid by the tissue resection. Typically, a carrier is disposed in an interior of the collector housing where the carrier is configured to (a) removably carry the collector vial and (b) move between (i) a first position where the inlet and outlet ends of the collector vial are aligned with the fluid inflow and outflow ports of the collector housing to allow fluid flow, filtration, and collection and (ii) a second position where at least the fluid inflow port of the collector housing is sealed to block fluid flow from the fluid outflow connector. As described in more detail hereinafter, the collector vial is removable from and replaceable to the carrier, permitting collection of tissue and cellular debris during a resection procedure.

In some instances, the collector housing will have at least one lateral opening configured to allow placement of the collector vial on the carrier and removal of the collector vial from the carrier.

In some instances, the collector comprises a positioning tray having a superior bracket and an inferior bracket, wherein the lateral opening is disposed between the superior bracket and the inferior bracket.

In some instances, the superior bracket has an inflow opening which seals to the inlet end of the collector vial when the collector vial is mounted on the tray and the inferior bracket has an outflow opening which seals to the outlet end of the collector vial when the collector vial is mounted on the tray. Typically, the tray in the first position aligns the inflow opening in the superior bracket with the inflow port of the housing to allow fluid flow into the collection vial and aligns the outflow opening in the inferior bracket with the outflow port of housing to allow fluid outflow from the vial to the waste fluid collection reservoir. Optionally, the tray in the second position may align the inflow opening in the superior bracket with a first solid surface of the collector housing to block fluid flow into the collection vial. Additionally the tray in the second position may align the outflow opening in the inferior bracket with a second solid surface of the collector housing to block fluid flow out of the collection vial.

In some instances, the collector vial comprises a transparent material to allow a user to view the tissue debris being collected in the collector vial during a procedure, typically by viewing the through the opening in the collector housing.

In some instances, the collector vial is exposed on opposing sides of the housing and configured for manual manipulation between the first position and the second position in the housing.

In a further aspect, the present invention provides a tissue removal system comprising a tissue removal device having a fluid outflow connector configured to direct waste fluid to a waste fluid collection reservoir and a tissue trap as in any of the embodiments described above.

In some instances, the tissue removal systems may further comprising a fluid management system for circulating fluid flow from a fluid source through the tissue removal device and fluid outflow connector to the waste fluid collection reservoir.

In a further aspect, the present invention provides a method for collecting tissue samples from a tissue resection fluid waste stream comprising directing the tissue resection fluid waste stream through a fluid inflow port of a collector housing. The tissue resection fluid waste stream is passed through an inlet end of a collector vial disposed at a first position in the collector housing, and tissue particles in the tissue resection fluid waste stream are collected on a filter in the collector vial. The collector vial may be positioned at a second position in the collector housing to block flow of the tissue resection fluid waste stream into the collection vial within the collector housing.

In specific instances of these methods, the collector vial is removably held on a carrier in an interior of the collector housing.

In specific instances of these methods, the carrier is pushed in a first direction within the housing to align the collector vial with the tissue resection fluid waste stream and allow the tissue resection fluid waste steam to flow through the collector vial.

In specific instances of these methods, the carrier is pushed in a second direction within the housing to seal the collector vial and prevent allow the tissue resection fluid waste steam from flowing through the collector vial.

In specific instances of these method, the collector vial may be removed from the carrier in the interior of the housing while the tissue resection fluid waste steam remains prevented from flowing through the collector vial.

In specific instances of these method, a new collector vial may be inserted onto the carrier within the interior of the housing while the tissue resection fluid waste steam remains prevented from flowing through the collector vial.

In specific instances of these method, the carrier may be pushed in the first direction within the housing to align the new collector vial with the tissue resection fluid waste stream and allow the tissue resection fluid waste steam to flow through the new collector vial.

In a further aspect, the present invention provides a tissue resection system comprising a tissue resecting device, a tissue collector, and a fluid management system. The fluid management system circulates fluid from a fluid source through the tissue removal device and outflow tubing to a waste fluid reservoir. The tissue collector is disposed in the outflow tubing and carries a removeable vial having a filter for collecting removed tissue. The vial is carried on a tray in the housing that is moveable between a first position and a second position such that the vial is removable from the tissue collector during usen. In this way, the tray functions as a valve to permit fluid flows through the vial in the first position and to block fluid flows into the vial in the second position.

In a still further aspect, the present invention provides an imaging and resecting device comprising a handle coupled to an elongated shaft extending about a longitudinal axis to a working end. A moveable electrode is carried at the working end, and a motor is configured to move the electrode to resect tissue. An image sensor is carried at the working end with field of view adapted for viewing the moveable electrode during use and first and second light-emitting diodes are also carried on the shaft, usually adjacent to the imaging sensor. The first LED is carried at the working end and has a wavelength of a white light for illuminating a working space. The second LED is carried at the working end and has a blue (ultraviolet) light wavelength, where the combination of white and blue light can enhance visualization of residual cancerous cells at the tissue margins after resection.

In yet another aspect, the present invention provides a method for resecting tissue from a tissue bed. The method comprises engaging a tissue resection element on a shaft against target tissue in the tissue bed, leaving a cavity in the tissue bed. An light sensitive imaging agent, such as hex-aminolevulinate HCl (Cysview®, Karl Storz) is delivered to exposed tissue in the cavity, and blue (ultraviolet) light and white light from illumination sources on the shaft simultaneously delivering to the exposed tissue. Cancerous cells exposed the combination of blue (ultraviolet) light and white light delivered from illumination sources on the shaft appear pink, indicating that cancerous tissue may remain and that further tissue resection or other therapies may be necessary In still further aspects, the present invention provides a tissue resecting device comprising a shaft assembly movably attached to a handle and having a longitudinal axis. A housing is secured to a distal end of the shaft and has a window configured to be fluidly coupled to a negative pressure source. An electrode is disposed in the housing and configured to move relative to the window, and a motor in the handle is adapted to move the electrode across the window.

In an additional specific example, the motor will be adapted to move the electrode at a fixed speed or rate relative to the window, e.g. at a rate greater than 1 cycle per second (CPS), often greater than 5 CPS.

The shaft may be operated manually. That is, the user may be able to manually initiate the at least one motor to move the electrode in the housing relative to the window and then manually reciprocate the shaft in an axial stroke relative to the handle. Even when being operated manually, the tissue resecting device will usually be operated through an interface (typically including a radiofrequency (RF) power supply) which may provide for specific operational parameters, often fixed or manually adjustable parameters, such as stroke times, power levels, RF waveforms, and the like, without having feedback control capability.

Often, the tissue resecting device will be provided as part of a tissue resecting system which further comprises a controller which is configured to operate not only the motor, but usually also a RF power source which is coupled to the electrode and also a negative pressure source which may be coupled to the window in the housing. The controller may be further configured or adapted to automatically or manually control at least one motor to stop movement of the electrode in a selected position relative to the window. Alternatively or additionally, the controller may be adapted to stop the electrode in the center of the window. Alternatively or additionally, the controller may be adapted to stop the electrode at an end of the window.

The controller may be adapted in a variety of other different control protocols. For example, the controller may be adapted to control the motor to provide a single movement cycle of the electrode back and forth across the window. That is, the user may be able to cause the controller to initiate only a single pass of the electrode over the window in order to achieve a controlled cutting of tissue. Additionally, the controller will usually be configured to control and coordinate the delivery of negative pressure from the negative pressure source to the housing window and to actuate the at least one motor, usually contemporaneously.

In still further aspects of the systems of the present invention, the controller may be configured to modulate the negative pressure source in response to movement of the electrode relative to the window. For example, the controller may be configured to active or deactivate the RF source in response to movement of the electrode relative to the window. Still additionally, the controller may be configured to activate or deactivate the RF source to deliver a cutting current waveform or a coagulation waveform to the electrode.

In particular aspects of the present invention as described in detail below, the devices, systems and methods are particularly configured for treating the prostate, optionally under endoscopic visualization. For example, the systems may comprise a RF source configured to deliver RF current alternatively in a cutting waveform and a coagulation waveform to the electrode, a motor configured to move the electrode, and a controller configured to operate the motor and RF source in a first mode delivering a cutting waveform while activating the motor to move the electrode in a second mode delivering a coagulation waveform after de-activating the motor to stop the electrode in a selected stationary position. Such methods for treating a bladder tumor or prostate tissue may comprise providing a treatment device with a shaft extending along a longitudinal axis to a distal portion having a window communicating with an aspiration source and a motor driven electrode adapted to move relative to the window. The window is engaged against targeted bladder tissue or prostate tissue, and the RF source is operated in a first mode with a cutting waveform delivered to the electrode while activating the motor to move the electrode to resect tissue and thereafter operated in a second mode with a coagulation waveform delivered to the electrode after de-activating the motor to stop the electrode in a selected stationary position to coagulate tissue.

In one particular aspect of the present invention, a tissue imaging and resection device comprises a handle and an introducer sleeve attachable to the handle. Typically, the handle will be permanently affixed to the introducer sleeve, but in other embodiments the handle and introducer sleeve could be detachable. The tissue imaging and resection device further comprises an axially translatable resecting component disposed within the introducer sleeve assembly. The axially translatable resecting component typically has a working end disposed at a distal end thereof where the working end usually includes an electrosurgical or other cutting implement configured to resect tissue. The tissue imaging and resection device will typically further comprise a tubular assembly disposed within the introducer sleeve and having an electronic imaging sensor, a lens, and a light source, disposed at a distal end of the tubular assembly.

In particular aspects of the tissue imaging and resection device, the handle will often carry a motor which is operatively coupled to the resecting component for driving a movable tissue resection element, such as an electrode, blade, or the like, in the resecting component. In specific embodiments, the tissue resection element comprises a radio frequency (RF) electrode of a type that can be connected to a radiofrequency power supply which delivers a cutting current to the electrode in order to allow the electrode to resect tissue as it is advanced there through. In such instances, the tissue imaging and resection device will typically include electromagnetic (EM) shielding between the electronic image sensor and the RF electrode. For example, the electronic image sensor and associated electrical leads may be encased in an electrically conductive tube, cylinder, or elongate hollow structure, typically a metal tube, which is covered with a polymeric or other electrically insulating layer, such as a shrink wrap tubing, over its exterior surface and a similar insulating layer over a lens component coupled to the image sensor.

In still further instances, the introducer sleeve of the tissue imaging and resection devices of the present invention will have a proximal and, a distal end, and a central passage extending along an axis between the proximal and distal ends. In these embodiments, the axially translatable resecting component typically comprises a shaft extending axially through the central passage of the introducer sleeve. The shaft will typically have a resection window near its distal end and an aspiration channel extending from the resection window to a proximal location on the shaft. The proximal location will usually lie within the handle and be configured for coupling to a negative pressure source via a connection in the handle.

In further specific instances, the tubular assembly may comprise at least one tubular member disposed in parallel to the shaft of the axially translatable resecting component within the central passage of the introducer sleeve. The tubular assembly may comprise a single tubular member which carries each of the electronic imaging sensor, lens, and the light source. More typically, however, the tubular assembly will comprise a first tubular member which carries the lens and the electronic imaging sensor and a second tubular member which carries the light source. By separating the imaging components from the light source, e.g., placing only the imaging sensor and associated conductor leads within one electromagnetically isolated structure as described above, and placing the light source in a tubular or other structure, the first and second tubular members may have a total cross-sectional area that is less than a single tubular member and such first and second tubular members may be isolated from one another by electromagnetic shielding to inhibit or prevent interference between the relatively high power light source and the low power imaging sensor. For example, the light source may comprise a light emitting diode (LED) at a distal end of the second tubular member with LED conductor leads extending from a proximal location on the second tubular member to the LED. The first tubular member may further comprise sensor conductors extending from a proximal location thereon to the electronic image sensor. In particular configurations, the sensor conductors are coupled to a circuit board, and all sides and a distal end of the first tubular member are encased in components providing electromagnetic shielding of the image sensor and sensor conductors. In such instances, at least a distal portion of the electromagnetic shielding in the field of view of the lens will be transparent of the lens may be configured to provide such shielding.

In still other specific instances of the tissue imaging and resection devices of the present invention, at least a portion of the second tubular member will be encased in electromagnetic shielding. In such instances, at least a distal portion of the electromagnetic shielding on the second tubular member will also be transparent in order to allow the projection of light from the light source there through.

In still other specific aspects, the present invention provides devices, tools, systems, and methods for electrosurgical treatment of tissue, particularly for performing urological procedures such as resecting prostate tissue, resecting bladder tissue, and the like. The devices and tools of the present invention can be made with very low profiles, typically with diameters or widths at or below 10 mm, often below 6 mm, and frequently as low as 4 mm or less. The low-profile devices and tools of the present invention are particularly advantageous as they can be configured to incorporate movable electrodes and other cutters, vacuum-assisted tissue extraction lumens, and other desirable features within the limited tool sizes available.

In one particular aspect, the tissue resection component, comprises an elongated shaft having an electrode assembly at or near a distal end thereof. The elongated shaft has a tissue-receiving window in a working end thereof, where the tissue-receiving window opens to a tissue-extraction lumen which extends along a longitudinal axis of the shaft. The electrode assembly includes a movable electrode which extends in a lateral direction over an exterior of the tissue-receiving window. The electrode assembly is configured to reciprocate the moveable electrode axially over an exterior region of the tissue-receiving window to resect tissue which is drawn inwardly into or through the window, typically by applying a vacuum or negative-pressure to the tissue extraction lumen. The moveable electrode has first and second lateral portions or sides that extend over first and second lateral edges of the tissue-receiving window, thus improving the ability of the electrode to resect or sheer tissue that is received through the window.

The moveable electrode may have a total exposed surface area which is very low, typically in the range from 0.05 in$^2$ to 0.30 in$^2$. In more specific aspects, the electrode has a surface area less than 0.30 in$^2$, often less than 0.20 in$^2$, and in some instances less than 0.10 in$^2$. In such embodiments, the window will typically have an open area in the range from 8 mm$^2$ to 16 mm$^2$.

In still other aspects of the present invention, the electrode assembly is configured to reciprocate the moveable electrode with a stroke that extends over proximal and distal edges of the tissue-receiving window. By thus having the movable electrode extend over both the lateral edges and the proximal and distal edges of the tissue receiving window, complete resection of the tissue can be achieved.

In still further specific aspects of the present invention, the electrode assembly comprises a sleeve disposed externally on the electrode shaft, typically over an axial path along an outer cylindrical surface of the shaft. A longitudinal wire member is mounted to reciprocate within a lumen of the external sleeve, and a distal end of the longitudinal wire is attached to or integrated with the first lateral portion of the moveable electrode. Exemplary movable electrodes may thus comprise a lateral extension of the longitudinal electrode wire, e.g., in a hockey stick configuration. As described in more detail below, the lateral extension will typically be curved so that the electrode follows a curved envelope defined by the window which may be in a cylindrical wall of the working end or often in a curved surface that is offset outwardly from the cylindrical surface of the shaft.

The working end of the device may further comprise a ledge adjacent the second lateral edge of the tissue-receiving window, and a distal tip of the second lateral portion of the moveable electrode may travel along a surface of the ledge as the moveable electrode is reciprocated.

In still further aspects of the present invention, the tissue-receiving window is formed in a curved surface of dielectric housing and such a curved surface is outward and asymmetric relative to a cylindrical surface of the shaft. The moveable electrode typically has an arcuate shape with a curvature that conforms to the curvature of the tissue-receiving window.

In still other specific aspects of the present invention, the tissue resecting devices may further comprise a handle attachable to a proximal end of the elongated shaft. The motor drive assembly is typically disposed within the handle. The motor drive assembly may be adapted to axially reciprocate the moveable electrode across the window in the range of 1 Hz to 50 Hz.

Typically, the tissue resecting devices of the present invention will be present in systems comprising a controller adapted to control the motor drive assembly, the negative pressure source, and energy delivery to the movable electrode.

In still other specific aspects of the present invention, the window edges may comprise a dielectric material. For example, the working end may comprise a dielectric housing with the tissue-receiving window disposed in the dielectric housing. In such instances, the lateral edges as well as the proximal and distal edges of the tissue-receiving window will be formed from the dielectric material. The dielectric material may be any one or more of a polymer, a ceramic, a glass, or other suitable dielectric materials.

DETAILED DESCRIPTION OF THE INVENTION

Figure 1:
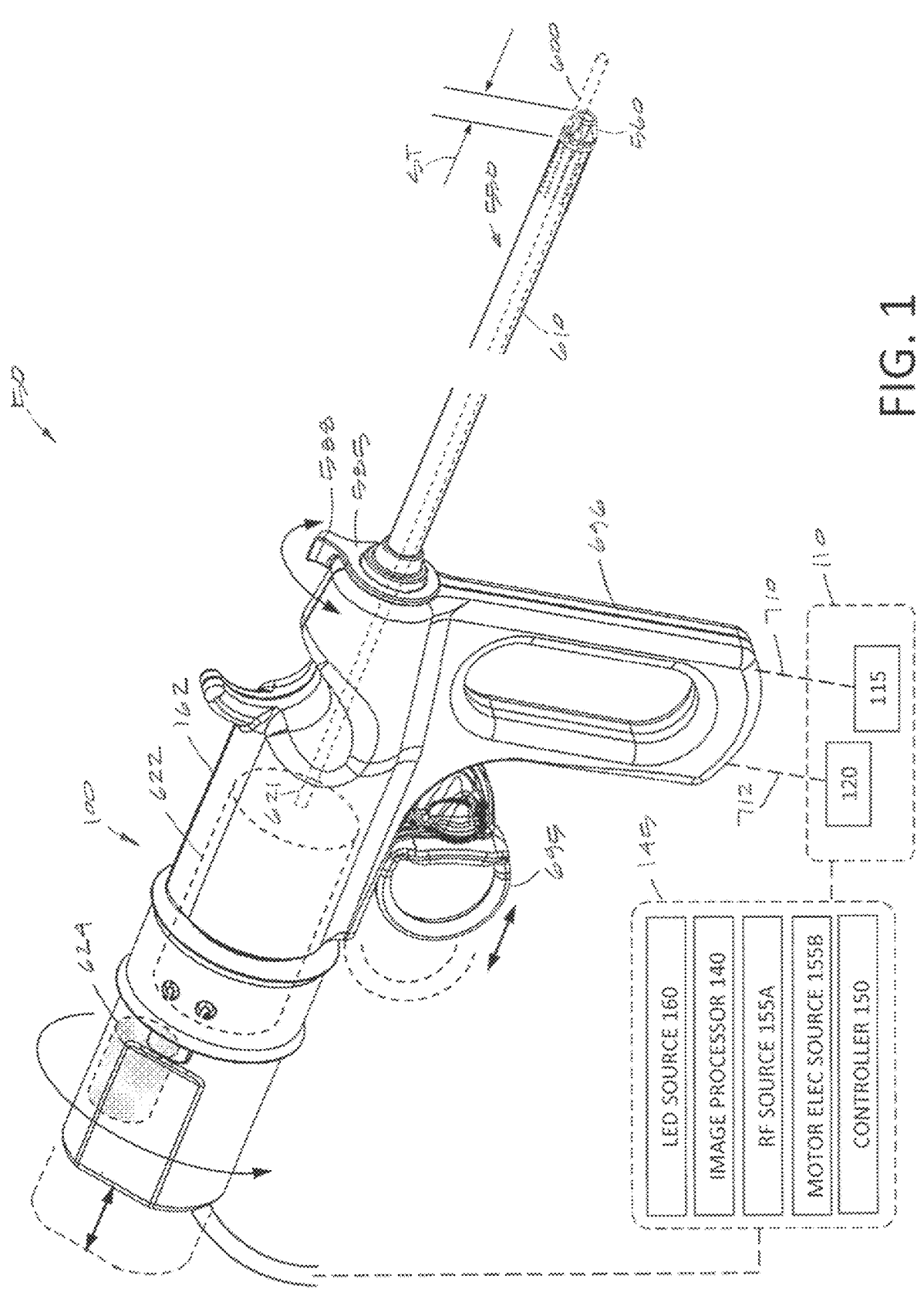
FIG. 1 is a view of a tissue resecting system and a block diagram of systems and operating components corresponding to the invention.
Figure 2:
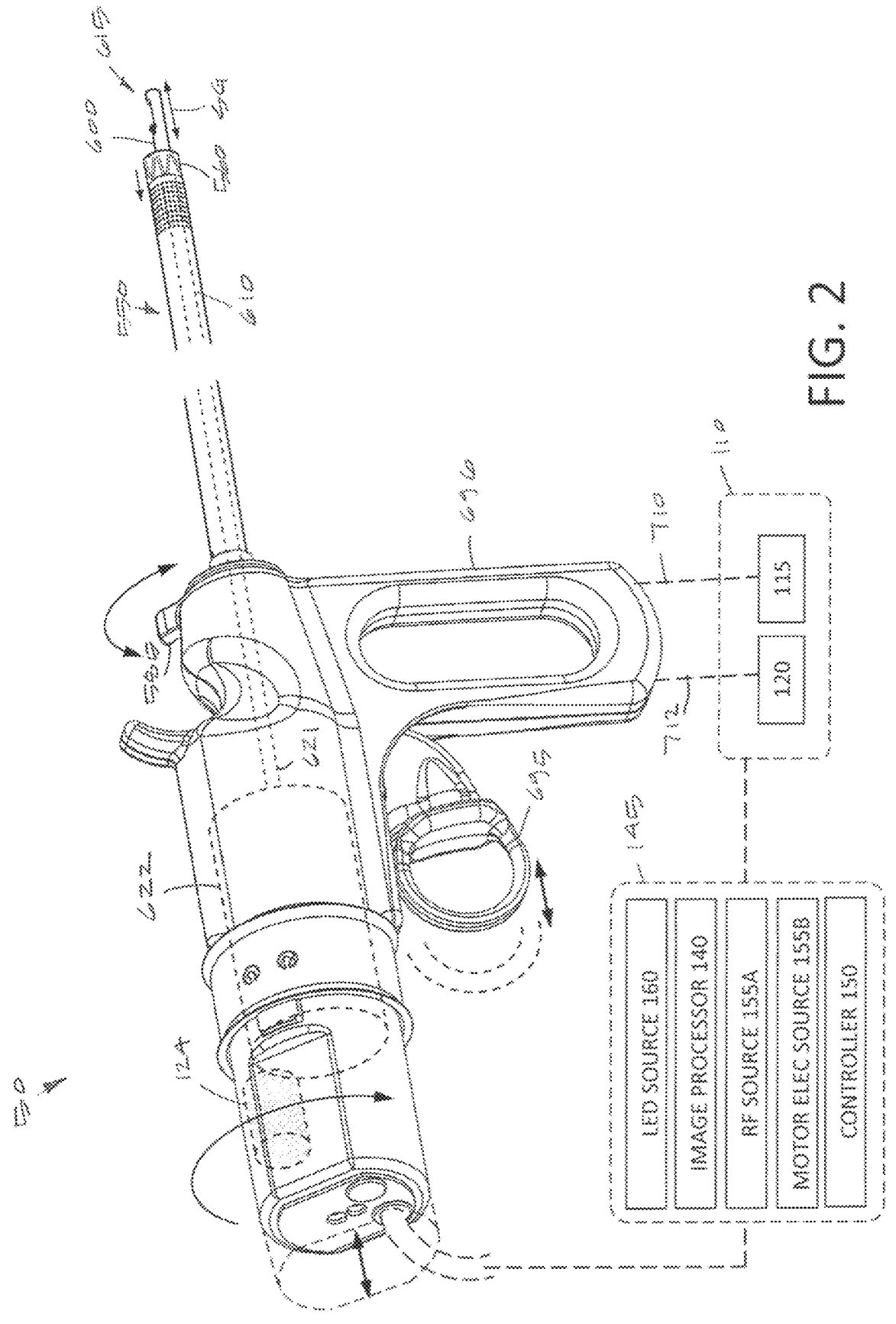
FIG. 2 is another perspective view of the system of FIG. 1 from a different angle showing the working end of a tissue-resecting component extending distally from an outer sleeve of the device.

FIGS. 1-2 illustrate an endoscopic, electrosurgical tissue resecting system 50 for use in urological procedures to resect tissue. The system 50 includes a hand-held resecting device 100 and fluid management system 110 consisting of a fluid source 115 for providing fluid inflows or irrigation to a working space and a negative pressure source 120 for aspirating fluids from the working space.

Figures 4A, 4B:
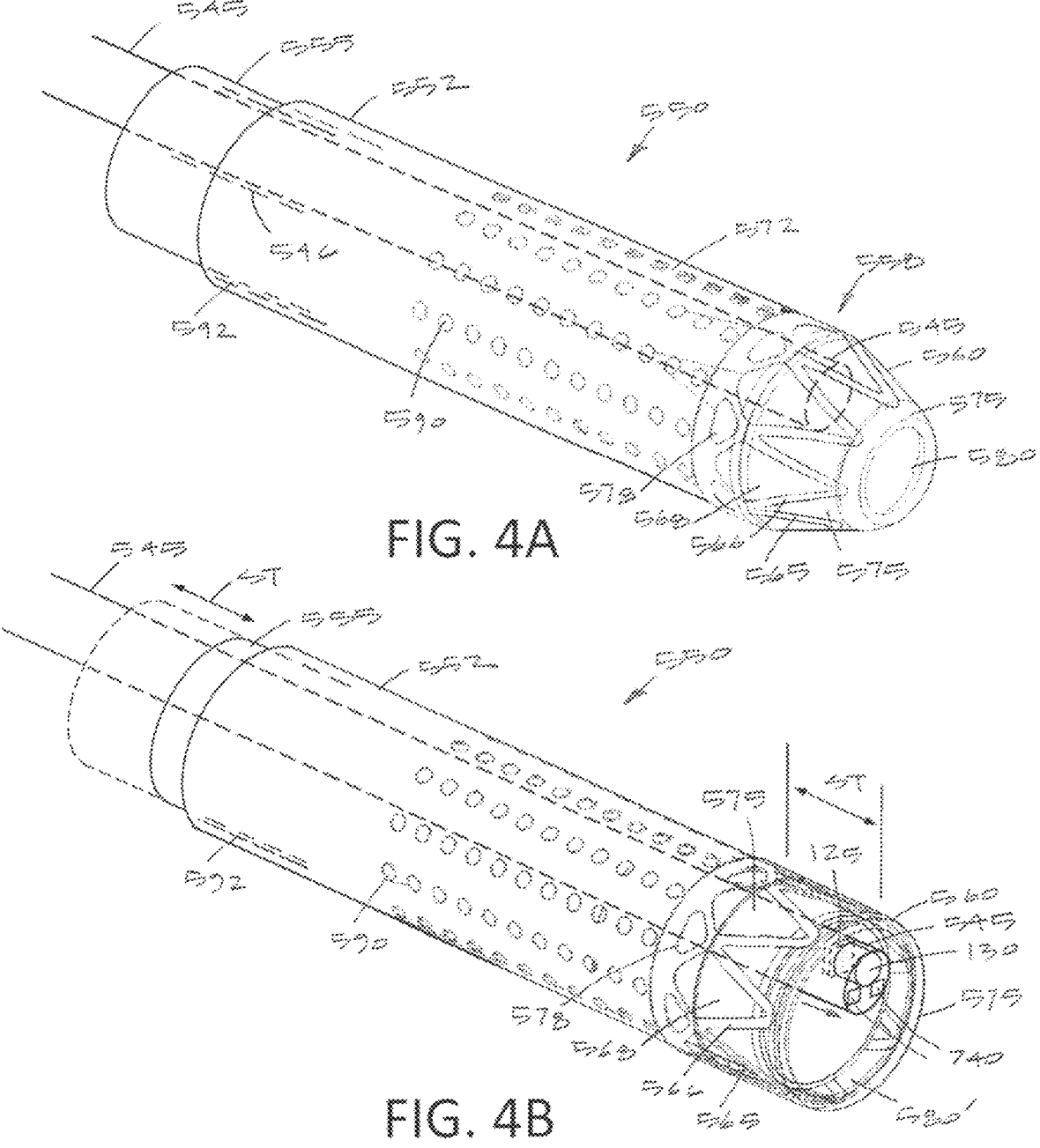
FIG. 4A is an enlarged view of the distal end portion of the resecting device of FIGS. 1-2 showing an expandable, resilient structure in a tapered shape for introduction into a patient's body.
FIG. 4B is another view of the distal end portion of the resecting device of FIG. 4A showing the resilient structure in a second, expanded cylindrical shape for introduction of a resecting component therethrough.

The resecting device 100 is a single-use tissue device or probe including a single-use viewing system consisting of a distal electronic imaging sensor 125 (with lens 130) coupled to an imaging processor 140 in a console or base unit 145 (see FIGS. 1 and 4A). The base unit 145 may optionally carry the fluid management system 110. Additionally, the base unit 145 may carry a microprocessor or controller 150 for controlling all operating parameters of the fluid management system 110, an RF source 155A for energizing the electrosurgical component, an electrical source 155B coupled to a motor drive unit described further below and an LED source 160 for delivering electrical current to at least one LED described further below.

The resecting device 100 has a handle portion 162 that is coupled to an elongated shaft or introducer sleeve assembly 550 that has an outer diameter ranging from about 5 mm to 10 mm, and in one variation is approximately 7 mm in diameter. In a variation, the device is adapted for performing a TURPT or TURP procedure where the shaft portion has a length suitable for introducing in a transurethral approach to reach the targeted prostate tissue or bladder tissue.

The tissue resecting system 50 includes four functional components which will be described separately. First, the system includes introducer sleeve component that has a soft tapered tip for introducing through body passageway under endoscopic vision wherein the sleeve can be adjusted to a cylindrical, non-tapered shape for advancing the resecting component therethrough. Second, the system 50 includes the RF tissue resecting component with a motor-driven moveable active electrode where the return electrode comprises a shaft of the tissue resecting component or any other conductive surface of the introducer sleeve assembly 550. Third, the system 50 includes the fluid management component 110 as indicated above. Fourth, the system includes an endoscopic viewing component.

As can be understood in FIGS. 1, 2, 4A-4B, the resecting device 100 has an integrated introducer sleeve assembly 550 which consists of an outer introducer sleeve or tubular member 552 and an inner sleeve 555 described further below. FIGS. 1-2 show the outer sleeve 552 fixed to the handle 162 which extends to a distal end 558 and which includes a resilient structure 560 that is movable or deformable between a first tapered, rounded-nose shape or configuration (FIG. 4A) for introduction through a body passageway and a second cylindrical shape or configuration (FIG. 4B) that allows for the endoscope sleeve 545 and resecting component 600 to be advanced into or through the distal end of the sleeve assembly 550 and resilient structure 560. The outer introducer sleeve 552 can be a thin-wall stainless steel material with a diameter ranging from about 5 mm to 10 mm.

In FIG. 4A, which is an enlarged view of the resilient structure 560 of FIGS. 1 and 2 in its tapered position, it can be seen that the structure 560 is in a repose, or non-tensioned and contracted configuration. FIG. 4B show the distal end 558 of the sleeve assembly and resilient structure 560 in a tensioned and expanded configuration.

In FIG. 4A, it can be seen that one variation of outer introducer sleeve 552 comprises a thin-wall metal tubing with a distal portion 565 that comprises a spring material that defines a plurality of spring struts 566 and openings 568 to allow movement of the structure 560 from the repose position of FIG. 4A to the tensioned position of FIG. 14B. In one variation, the struts 566 define triangular shapes around openings 568 and the struts can range in number from about 4 to 20 or more. In a typical embodiment, the struts 566 are fabricated by cutting the thin-wall tubing of a spring material and then forming the struts 566 into the repose shape as shown in FIG. 4A. In another variation, the struts can be formed from a round, flat or oval spring-type wire elements. The spring elements then can be welded or otherwise bonded to the distal end 570 of the rigid sleeve portion indicated at 572.

As can be further seen in FIGS. 4A and 4B, the resilient structure further comprises an elastomeric material 575, such as silicone, molded over the struts 566. The distal end 572 of the rigid sleeve portion is provided with apertures 578 therein for engaging the over-molded elastomer. In one variation, the elastomer 575 is a substantially transparent material to allow viewing therethrough. In other variations, the elastomer or polymer material may be opaque or non-transparent. The tapered shape of the resilient structure 560 in FIG. 4A is configured with a distal opening 580 that has a selected dimension that may range from 10% to 50% of the diameter of the opening 580' of the structure 560 in its expanded shape as shown in FIG. 4B. The dimension of the distal opening 580 in the tapered position of FIG. 4A is selected to allow viewing therethrough with the imaging sensor 125 during insertion of the distal end of the device 100 through a body passageway.

As can be seen in FIGS. 4A and 4B, in one variation the endoscope sleeve 545 can be in a proximal position when the resilient structure 560 is in its contracted, tapered configuration and then the endoscope can be move distally when the resilient structure 560 is in its open, tensioned position as shown in FIG. 4B.

Figure 3:
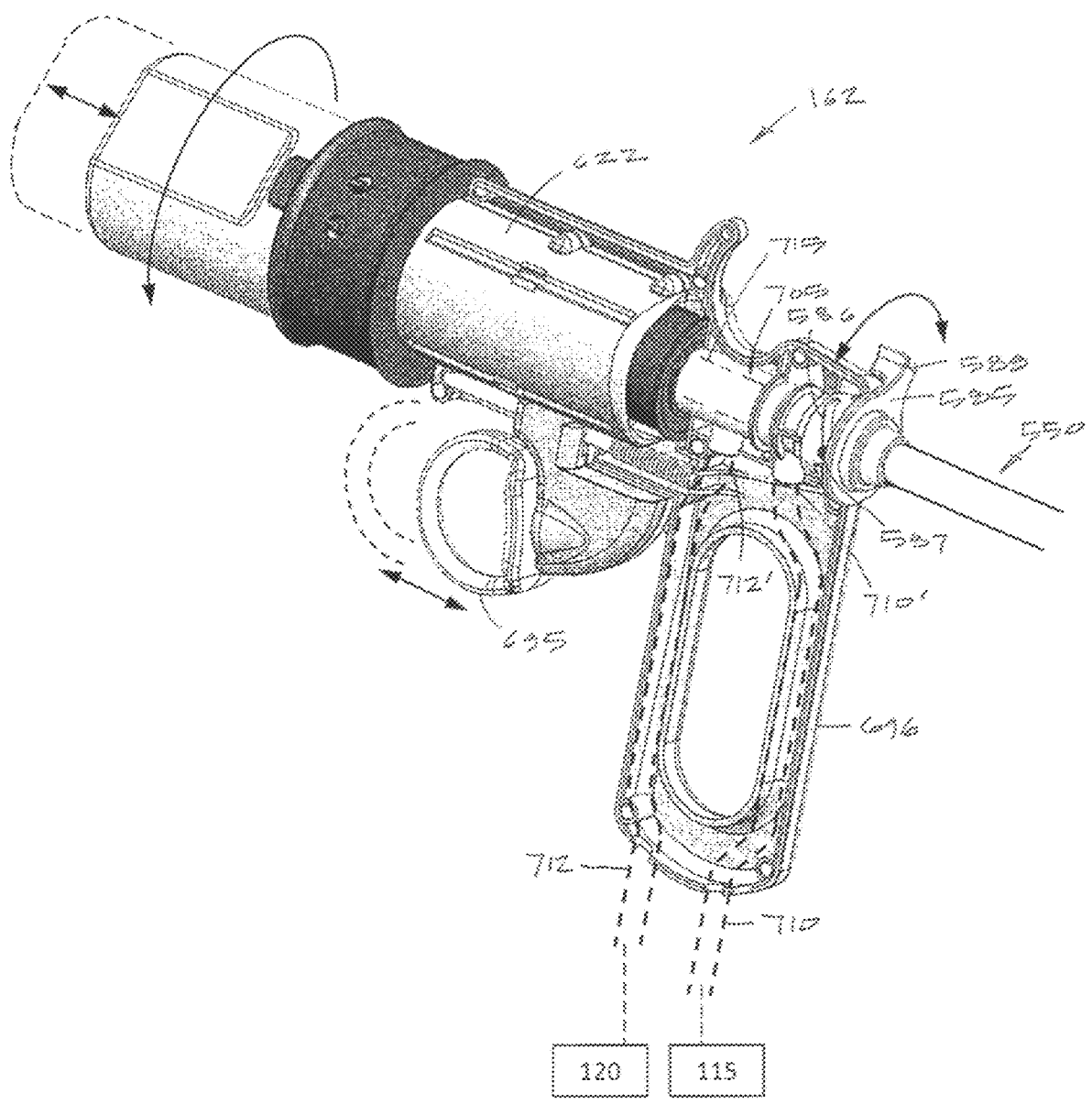
FIG. 3 is a perspective view of a handle of the resecting device of the system of FIGS. 1-2.
Figure 5:
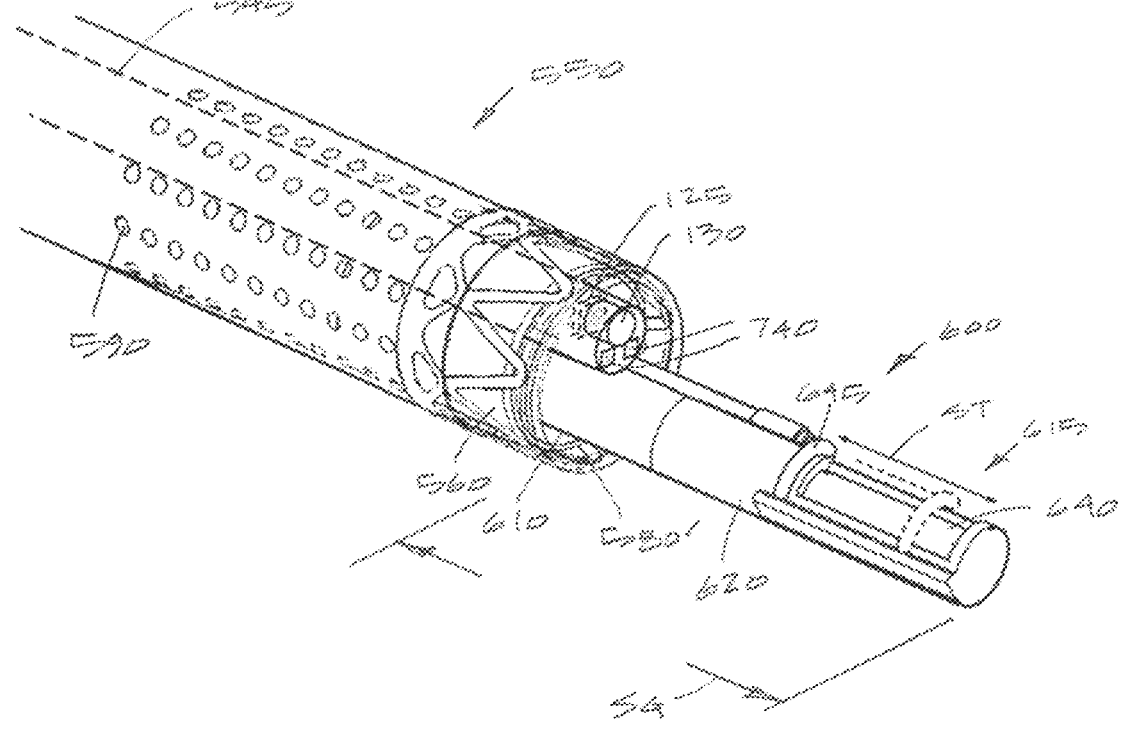
FIG. 5 is a view of the distal end portion of FIG. 4B in its expanded cylindrical shape with a resecting component extending distally beyond the resilient structure.

FIGS. 1-3 show the mechanism for moving the resilient structure 560 from the tapered, contracted position of FIG. 4A to the cylindrical position of FIG. 4B. In FIG. 3, it can be seen that the introducer sleeve assembly 550 includes the inner sleeve 555 that is adapted to move axially from a retracted position to the extended position as shown in FIGS. 4B and 5. In other words, the distal movement of the inner sleeve 555 will contact the inner surfaces 582 of the struts 566 and elastomeric material 575 in the tapered position of FIG. 4A and then push the struts 566 outwardly and stretch the elastomeric material 575 to provide the cylindrical shape of FIGS. 4B and 5 as the inner sleeve 555 is fully extended. FIG. 4B shows that the stroke ST of inner sleeve 555 can range from about 5 mm to 20 mm in a typical embodiment.

Figure 9:
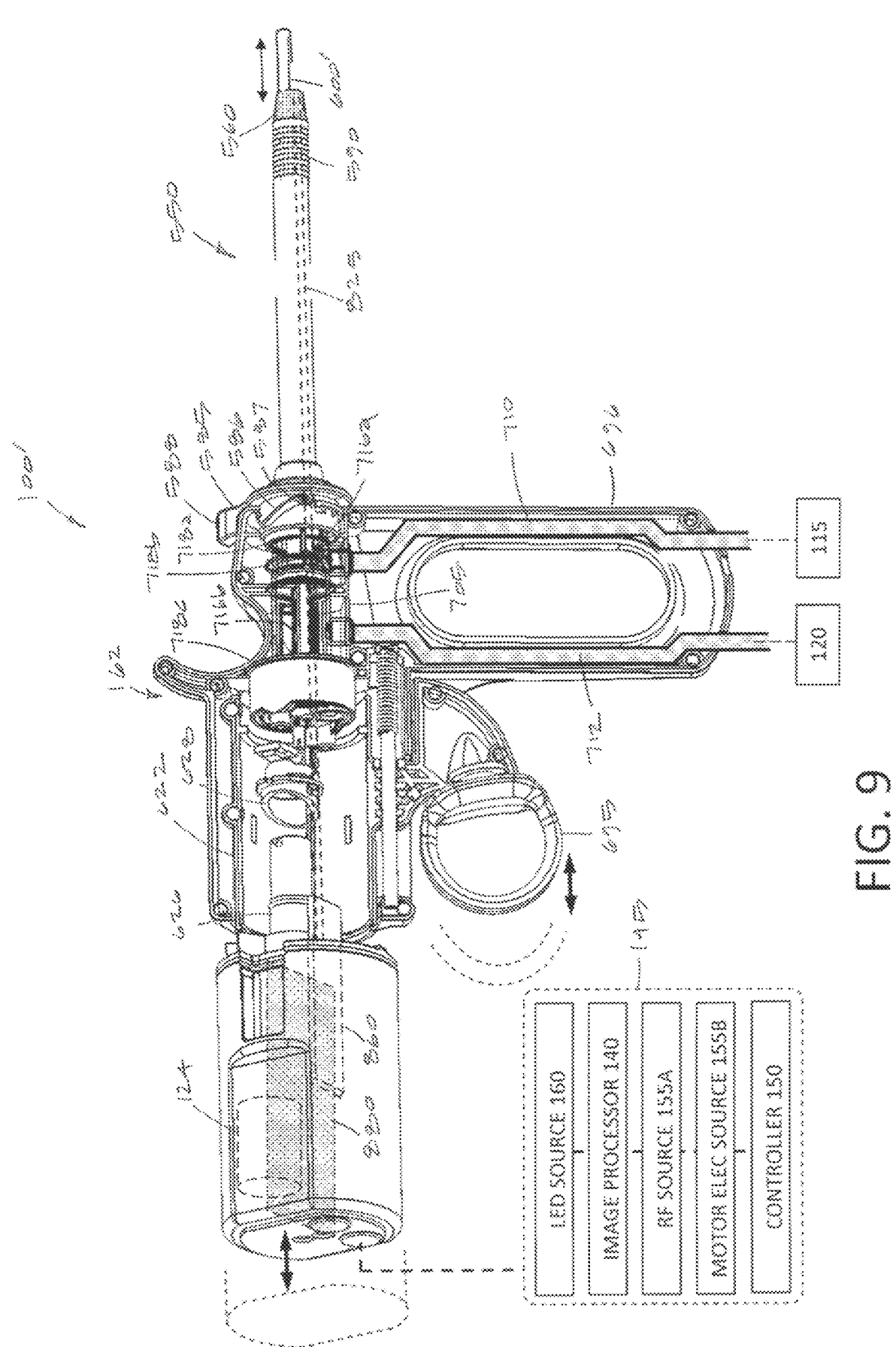
FIG. 9 is a perspective view of a handle of another resecting device that is very similar to that of FIGS. 1-2 except the working end or the tissue-resecting component is different and is shown in FIG. 10.

Referring to FIGS. 1, 3 and 9, the mechanism for moving the inner sleeve 555 from its retracted position to its extended position of FIG. 4B can be understood. In FIGS. 3 and 9, it can be seen that a rotating actuator element 585 is provided which has a cam surface 586 which interfaces with an element 587 of the inner sleeve 555 to move the inner sleeve 555 axially back and forth upon rotation of the finger tab 588 as indicated by arrow AA in FIGS. 1-3. Thus, the finger tab 588 can be designed to move from approximately 45° to 90° to move the inner sleeve 555 in the desired stroke ST as shown in FIG. 4B.

Figure 6:
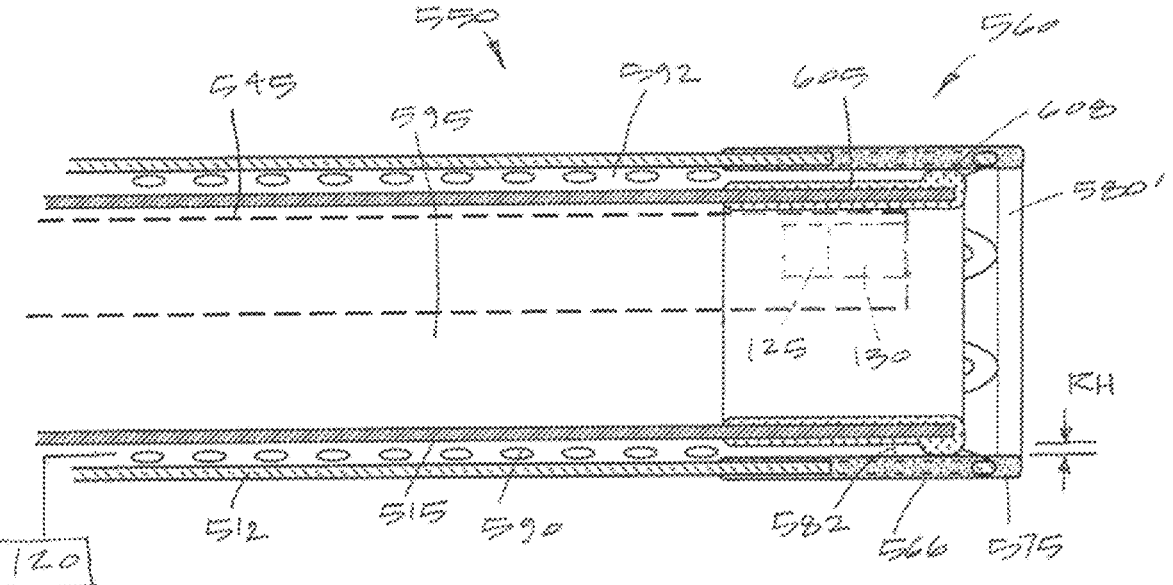
FIG. 6 is a sectional view of the distal end portion of the resecting device and resilient structure of FIG. 4B taken along line 6-6 of FIG. 4B.

Now turning again to FIG. 4A, in another aspect of the invention, the outer introducer sleeve 552 is configured with a plurality of ports 590 which communicate with the annular space 592 between the outer sleeve 552 and the inner sleeve 555 (see FIG. 6). In one variation, the annular space or outflow channel 592 between the inner and outer sleeves 552, 555 communicates with the negative pressure source 120 and thus provides an outflow path for distention fluid which may be independent of the flow channel through the resecting component 600. In the variation shown in FIGS. 4B and 5, the sleeve assembly 550 has a fluid inflow channel 595 that comprises the space outward of the shaft 610 of the resecting component 600 and within the inner sleeve 555.

In FIG. 6, it can be seen that the distal portion of the inner sleeve 555 includes a polymer over-molded portion 605 (e.g., silicone) which serves two purposes. First, the polymer over-molded portion 605 has an annular ridge 608 which interfaces with the inner surfaces 582 of the struts 566 and elastomeric material 575. The radial height RH of the annular ridge 608 thus provides the annular space 592 between the outer surface of the inner sleeve 555 and the inner surface of the outer sleeve 552 through which distention fluid may be aspirated after flowing through the multiple ports 590 in the outer sleeve 552. Secondly, the annular ridge 608 of the over-molded polymer portion 605 can be adapted to seal the interface between the inner sleeve 555 and the resilient structure 560 so that distention fluid is not aspirated through the distal opening 580' of the resilient structure 560 in its cylindrical shape as shown in FIG. 6. This aspect of the invention may be useful to prevent any interference with inflows of distention fluid through inflow channel 595. Rather, the variation shown in FIGS. 5 and 6 allows for fluid inflows to exit the resilient structure 560 and opening 580' around the distal end of the endoscope sleeve 545 which provides the advantage of clearing the visual field distal to the endoscope sleeve 545 to thereby maintain clear viewing. If both inflows and outflows were adjacent to one another in the interior of the resilient structure 560, the clearing of the visual field with fluid inflows could be impaired. In another variation (not shown), the annular ridge 508 could be provided with notches to allow a portion of the fluid outflows into annular space 592 to flow through the distal opening 580'. In a typical embodiment, the negative pressure source 120 would communicate with both the annular space 592 and the aspiration channel 525 in the resecting component 600.

Figure 7:
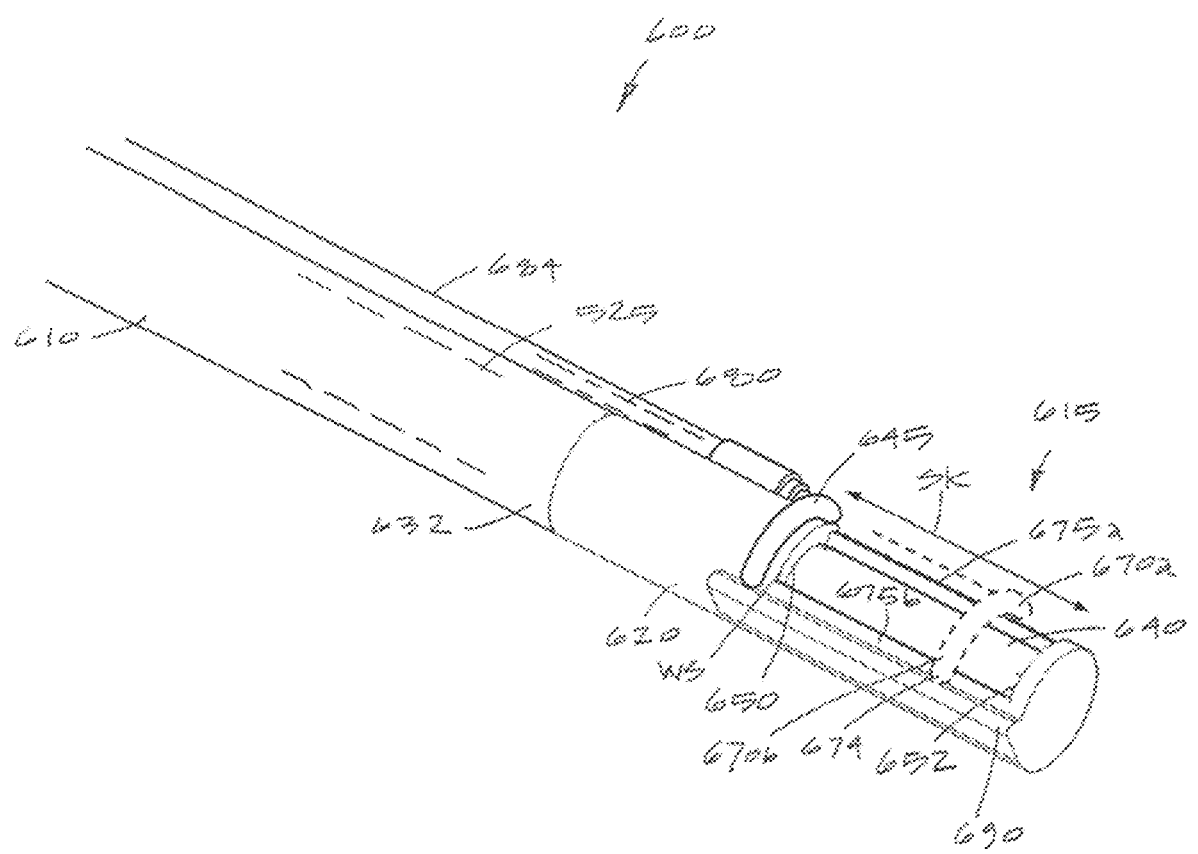
FIG. 7 is a perspective view of the working end of a shaft of the tissue-resecting component also shown in FIG. 2, the component having a distal dielectric housing and a reciprocating electrode that is adapted to move axially across the outer surface of a tissue-receiving window.
Figure 8:
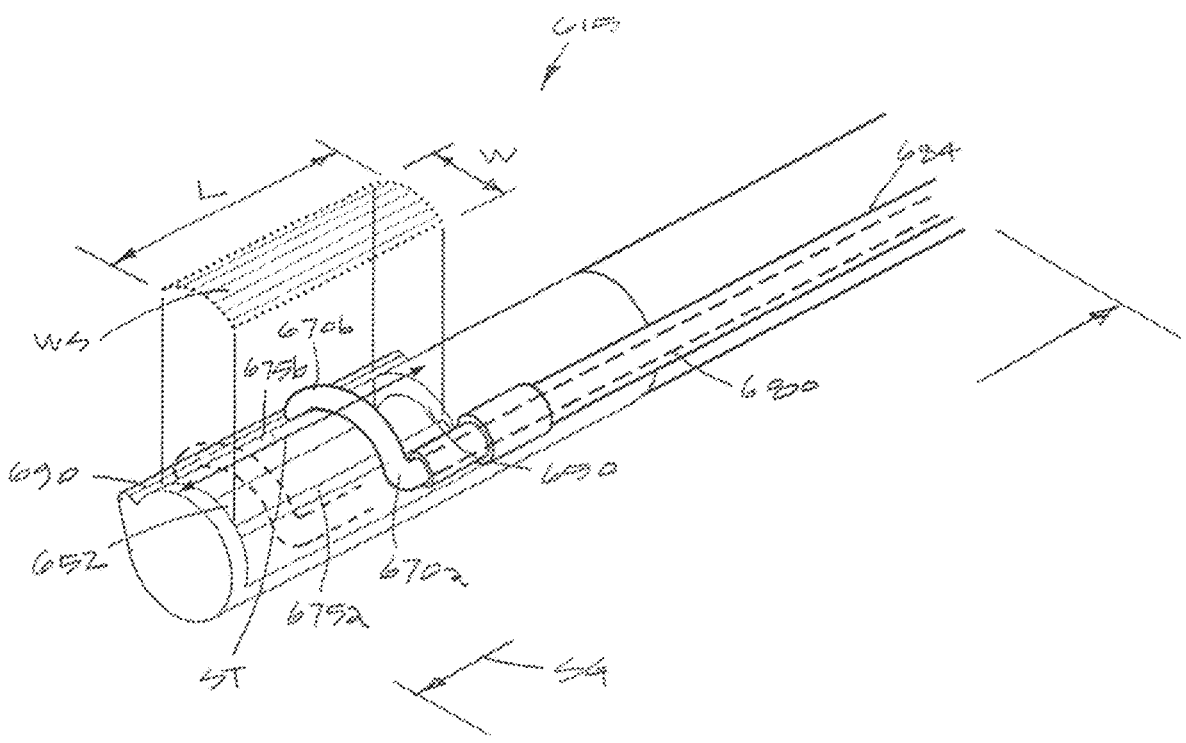
FIG. 8 is another perspective view of the working end of FIG. 7 from a different angle.

FIGS. 5, 7 and 8 illustrate an electrosurgical tissue-resecting component 600 that is carried in the introducer sleeve assembly 550. The elongated shaft or extension portion 610 has an outer diameter ranging from about 2 mm to 6 mm, and in one variation is about 4 mm to 5 mm in diameter. The shaft 610 extends about its central longitudinal axis 612 to its working end 615 that typically comprises a dielectric housing 620 as can be seen in FIGS. 7 and 8.

The proximal end 621 of the shaft 610 is coupled to the rotatable core 622 shown in FIGS. 1 and 2. A motor drive unit 624 shown in FIGS. 1 and 2 is adapted to reciprocate the electrode 645 as will be described further below. The reciprocation mechanism can be of any type known in the art and FIG. 9 shows a rotating drive sleeve 626 coupled to the motor drive 124 that has a surface (not shown) that rotates against a cam surface 628 coupled to a elongate shaft element connected to the electrode 645. It should be appreciated that the core 622 can be rotated 360° within the handle 162 which will not only rotate the resecting component but also rotate the image sensor 125 positioned at the distal end of the introducer sleeve assembly 550.

Referring to FIG. 7, in general, it can be seen the working end 615 includes the distal end portion 632 of shaft 610 that is coupled to the dielectric housing 620 which has a curved or part-cylindrical surface that has a tissue-receiving window 640 therein. A moveable electrode 645 is adapted to be driven by a motor drive unit 624 in the handle 162 (see FIG. 1) so that the curved electrode 645 can reciprocate across the window 640 from a proximal window end 650 to a distal window end 652 to thereby electrosurgically resect tissue that is captured in the window 640. The targeted tissue can be suctioned into and captured in window 640 by means of a negative pressure source 120 operated by controller 150 that communicates with a tissue extraction channel or aspiration channel 525 extending through the shaft 610 and connects to the window 640.

FIGS. 7 and 8 illustrate the dielectric housing 620 that can comprise a ceramic material such as zirconium oxide, aluminum oxide, silicon nitride or similar materials as are known in the art. Alternatively, the dielectric housing 620 can comprise at least in part a polymer or a glass material. In FIGS. 7-8, it can be seen that window surface has a curvature from side to side that can generally can match the diameter of shaft 610. Correspondingly, the electrode 645 is curved to cooperate with the window surface wherein an inner electrode surface has a radius ranging from 1 mm to 3 mm.

As can be further be seen in FIGS. 7-8, the width W of the window 640 can range from about 2 mm to 6 mm and the window length L can range from about 4 mm to 10 mm. Referring to FIGS. 7-8, one variation of tissue-resecting component 605 has an electrode 645 that can be tungsten or stainless steel wire that with curved electrode adapted to reciprocate across the window 640 at any suitable rate and in an embodiment can range from 10 to 20 Hz or more.

Referring to FIG. 8, in one variation of dielectric housing 620, it can be seen that the electrode 645 has a first lateral side 670a and a second lateral side 670b that extends to electrode tip 674. Thus, when moving axially, the lateral sides 670a and 670b of electrode 145 extend across the lateral sides or edges 675a and 675b of the window 640 to ensure that any tissue captured in the window is resected as the electrode 645 passes the window edges to function like a shear to resect tissue in a scissor-like manner. Further, the stroke SK is adapted cause the electrode 645 to reciprocate across the proximal window end 650 and the distal window end 652 as described above to electrosurgically shear tissue captured in window 640.

Referring to FIG. 7, the electrode 645 is coupled to wire shaft member 680 that extends through sleeve 682 that comprises a portion of the outer surface of shaft 610. The wire shaft member 680 is covered with an insulator sleeve 684 to thus provide an active electrode 645 with limited surface area which lower RF power requirements. The device can include a footswitch or finger switch (not shown) for activating the device wherein such activation would energize the electrode 645 from RF source 160 and also activate the motor drive 624.

Referring again to FIG. 3, the housing 620 is configured with a ledge 690 adjacent the lateral edge 675b of the window to receive and abut the distal tip 674 of electrode 645 as it reciprocates. The ledge 690 is adapted to prevent the electrode tip 674 from being snagged or caught in tissue.

FIG. 5 shows the introducer sleeve assembly 550 and the resilient structure 560 in its expanded position with the working end 615 of the resecting component 600 advanced through the distal the opening 580' in the resilient structure 560. As can be understood from FIGS. 2 and 5, the working end of the resecting component 600 is axially movable over stroke SG by means of actuating the thumb grip 695 axially relative to the fixed pistol grip portion 696 of the handle 162 (FIG. 2). At the same time, electrode 645 can be reciprocated to resect tissue as a physician axially and/or rotationally moves the working end 615 of the resecting component 600.

FIG. 8 shows working end 615 of the resecting component 600 from a different angle. In this variation, it can be seen that the window 640 of the working end defines the window surface WS or curved plane across which the electrode 645 reciprocates and cuts tissue. In this variation, the window 640 has a substantially large surface area WS for interfacing with targeted tissue, and the reciprocating electrode 645 in a typical procedure can provide a tissue removal rate that is greater than 5 grams per minute.

As can be understood from FIGS. 1 and 2, the fluid management component 110 includes a fluid source 115 and the negative pressure source 120. Typically, the fluid source comprises a saline bag and a peristaltic pump (not shown) controlled by the controller 150 for providing pressurized inflows into a working space. The negative pressure source 120 is provided typically by a second peristaltic pump controlled by the controller 150 to aspirate fluid and tissue chips through the device into a collection reservoir. Such systems are known in the art and need not be described further herein.

FIGS. 1, 3 and 9 illustrate the inflow and outflow pathways in the interior of the resecting device 100 or 100' which are coupled to the inflow and outflow pumps of the fluid management component 110 (FIG. 1). As can be seen in FIGS. 3 and 9, a flow channel housing 705 is provided in the handle 162 which includes means for allowing rotation of the rotating core 622 while maintaining the inflow and outflow channels in the sleeve assembly 550 in communication with inflow tubing 710 and outflow tubing 712. It can be seen in FIGS. 3 and 9 that the rotating shaft portion 715 within the flow channel housing 705 includes annular channels 716a and 716b with seals 718a, 718b and 718c therebetween, wherein annular channel 716a communicates with the inflow tubing 710 connected to housing 705 and further communicates with the inflow channel 595 in the sleeve assembly 550 (FIG. 6). Annular channel 716b communicates with the outflow tubing 712 connected to housing 705 and further communicates with the outflow channel 592 in sleeve assembly 550 (FIG. 6). Thus, it can be understood that the rotating shaft portion 715 within the flow channel housing 705 allows for fluid inflows and outflows as the core 622 core is rotated.

Now turning to FIGS. 4A and 5, the endoscopic viewing component comprises the distal imaging sensor 125 and lens 130 carried at the end of the endoscope sleeve 545. The endoscope sleeve 545 typically may be axially translatable within the shaft as shown in FIGS. 4A-4B. The mechanism for advancing the endoscope sleeve 545 can be thumb grip 695 which advances the endoscope sleeve 545 a predetermined distance and then stops its advancement. Further advancement and retraction of the thumb grip 695 then is adapted to translate the working end 615 of the resecting component 600 back and forth. In one variation, the endoscope sleeve 545 comprises a thin-wall tubular member of a (e.g., a metal or polymer) with the image sensor 125 and lens 130 positioned in a distal end thereof. A plurality of electrical conductors 722 are carried in passageway 724 of the sleeve 545 that are coupled to the image sensor 125. The conductors 722 can be in a flex circuit or can be in any suitable cable. Such conductors 722 carry signals from the image sensor to the image processor 140 which is in the base unit 145 but optionally can be carried in the handle 162. The entire sleeve 545 and lens 130 is encased in an insulator coating or shielding 725 that has sufficient insulative strength to shield the image sensor 125 and signals carried. by conductors 722 from any potential electrical interference from RF current carried to the working end of the resection device or from current carried to the motor 124. The insulator coating 725 is a type that is transparent for covering the lands 130 to allow viewing therethrough. In one variation, the insulator coating 725 extends over the entire length of the sleeve 525 as well as over any length of the conductors 722 that extend through the handle 162. The image sensor 125 may be any electronic imaging chip known in the art with a suitable lens 130 which are available, for example, from OmniVision, 4275 Burton Drive, Santa Clara, CA 95054 such as a High Definition Sensor used in cell phones and laptops.

In one variation, still referring to FIGS. 4B and 5, the endoscopic sleeve 545 further includes at least one LED 740 or other light source carried at the distal end of the sleeve. Of particular interest, the rotating core 622 is adapted to carry the image sensor 125 and the LEDs 740 together with the resecting component 600 thus allowing 360° rotation. Electrical leads 742 are also carried in the passageway 724 of the sleeve 545 which extend to LED source 160 (FIG. 1). The shielding 725 described above also protects the LEDs from interference by the RF source or motor source.

Figure 10:
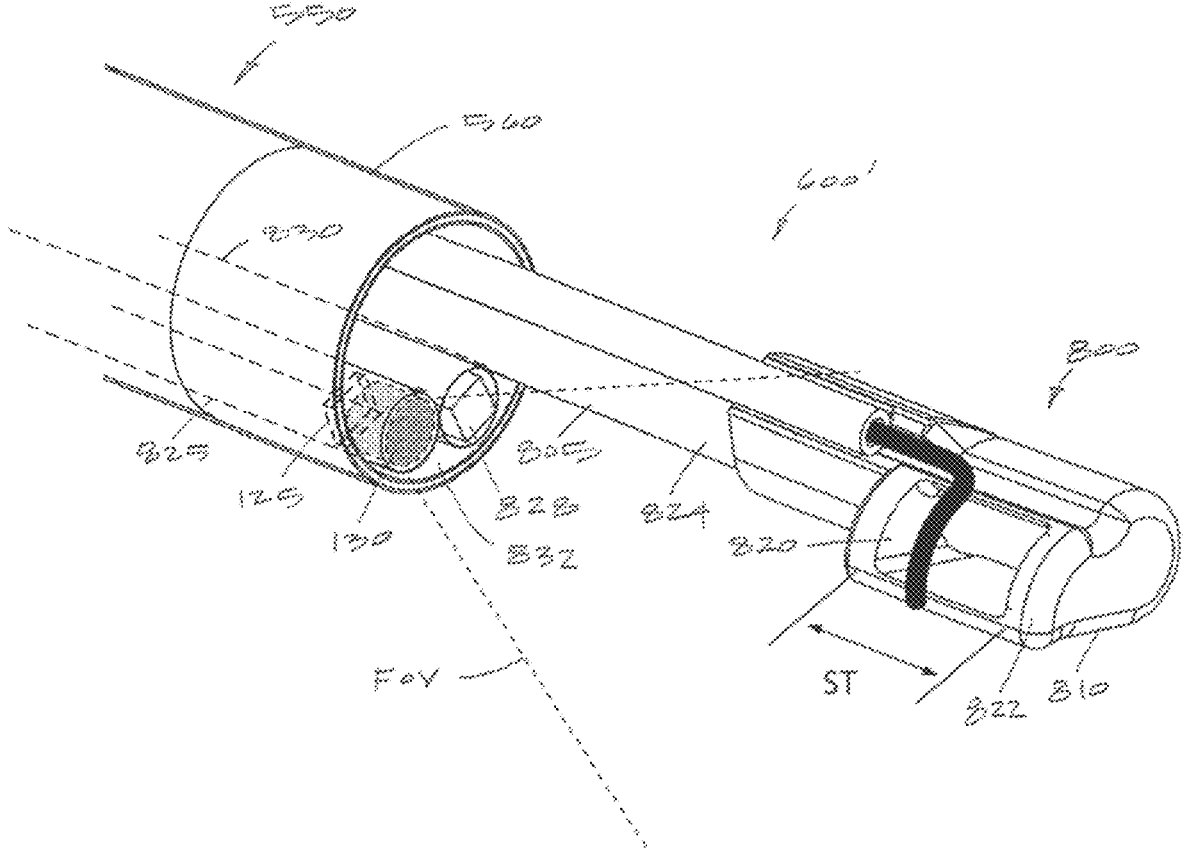
FIG. 10 is a perspective view of the variation of a working end of a tissue-resecting component of FIG. 9 with a reciprocating electrode.

Now turning to FIGS. 9 and 10, another variation of resecting device 100' is shown which is similar to that of FIGS. 1-6 except the resecting component 600' has a different variation of a working end 800. The working end 800 of the RF tissue-resecting component 600' again has an elongated extendable shaft 805 that carries a dielectric housing 810 with a reciprocating electrode 815 (see FIG. 10). In this variation, the dielectric housing 810 which carries the window 820 has an offset portion 822 that extends outward from the cylindrical surface 824 of the elongated shaft 805 the resecting component. In this variation, the offset window 820 and electrode 815 allows for improved endoscopic viewing of the electrode 815 when being reciprocated. The stroke of the electrode 815 is indicated at ST which is then easily observed within the field of view FOV (see FIG. 10).

FIG. 10 further shows that the image sensor 125 and lens 130 are carried in a first independent tubular sleeve 825 in this variation. Similarly, the single LED 828 is carried in a second independent tubular sleeve 830 in the introducer sleeve assembly 550. The use of independent sleeves 825 and 830 allow for compact design while still allowing for a fluid outflow channel 832 which comprises the space around the sleeves 825, 830. In a variation, the electrically conductive sleeve 825 extends into the handle and is covered with a dielectric layer, such as a heat shrink tubing. The electrically conductive sleeve 825 functions as shielding from electrical interference from the electrosurgical component while the dielectric layer electrically isolates the sleeve from the fluid environment. The electrical conductors within the sleeve 825 can consist of at least one co-axial cable with dielectric layers around each conductor or it can comprise a flex circuit.

Now turning to FIGS. 11A-15, another variation of working end 1000 of an imaging and resecting system 1005 is shown which is similar to that of FIGS. 9-10 except that the working end 1000 includes a sensor sleeve 1010 that carries both an image sensor 1015 within a housing together with an illumination source comprising an LED 1018. The term image sensor 1015 as used herein describes a CMOS chip and lens in a housing.

Figures 11A, 11B:
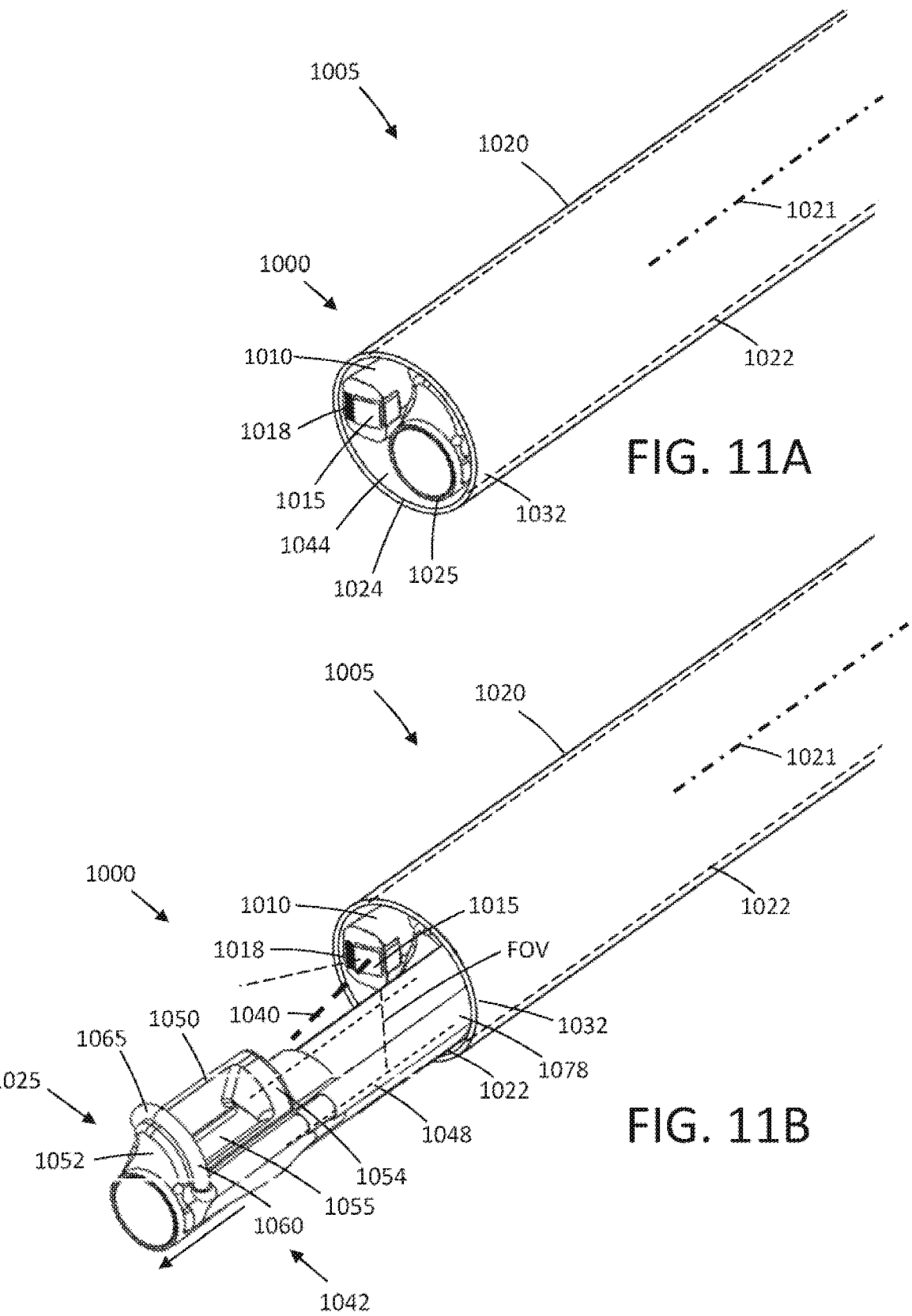
FIG. 11A is a perspective view of a working end of a imaging and resecting device similar to that of FIGS. 9 and 10 showing the endoscopic imaging component and resecting component in an outer sleeve in a position adapted for introduction into a body passageway.
FIG. 11B is a perspective view of the working end FIG. 11A with the resecting component extended from the outer sleeve in a deployed position.

More in particular, referring to FIGS. 11A and 11B, a variation of the working end 1000 has thin-wall outer sleeve 1020 with longitudinal axis 1021 that is similar to that described in previous embodiments with an interior passageway 1022 extending therethrough to a open distal end 1024, where the passageway 1022 carries the extendable resecting component 1025 of the device as well as a single elongated sensor sleeve 1010 that carries the image sensor 1015 and LED 1018.

Figure 12:
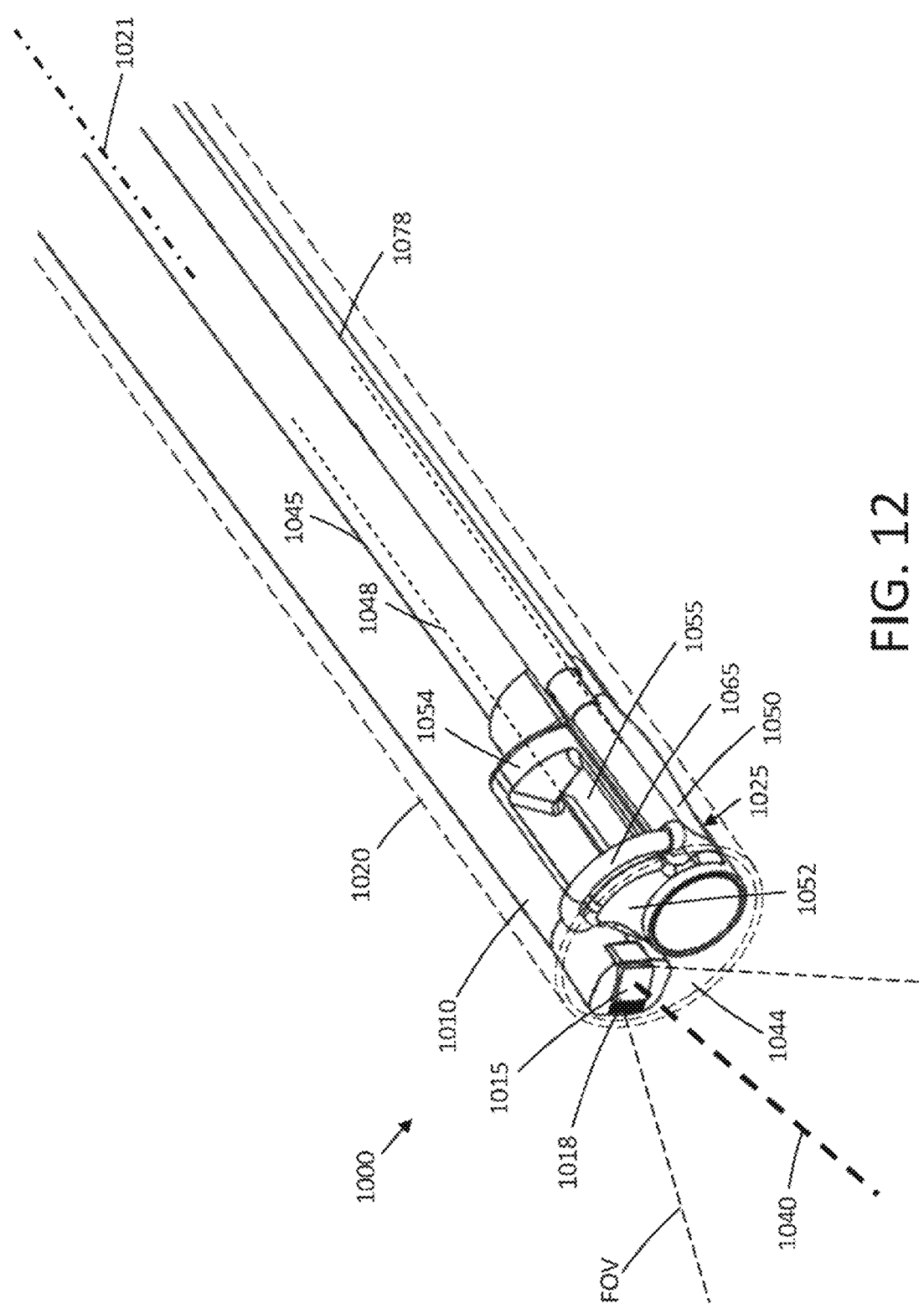
FIG. 12 is another view of the working end of FIGS. 11A and 11B with the outer sleeve in phantom view to show the nesting of components is the outer sleeve.

In FIG. 11A, it can be seen that the resecting component 1025 is in a retracted position relative to outer sleeve 1020, which is the position adapted for introduction of the device into a body passageway. In FIG. 11B, the resecting component 1025 is extended outwardly from the open distal end 1024 of passageway 1022 in the outer sleeve 1020 while the sensor sleeve 1010 remains in fixed position. It should be appreciated that the distal end 1032 of outer sleeve 1020 can carry a flexible, atraumatic tip of the type shown in FIGS. 4-6 above, but which is not shown in this variation for convenience. Referring again to FIG. 11B, it also should be appreciated that the sensor sleeve 1010 can be advanced slightly outward from distal end 1024 of the passageway 1022, or the outer sleeve 1020 can be retracted as described above in other embodiments that include the atraumatic tip of FIGS. 4 to 6. In FIGS. 11B and 12, it can be seen that the optical axis 1040 of the image sensor 1015 is angled relative to the outer sleeve axis 1021 or so that the field-of-view FOV is adapted to observe the working end 1042 of the resecting component 1025 during use. In other variations, the optical axis 1040 can be aligned with the axis 1021 of the outer sleeve 1020 where the field of view FOV is broad so as to view the working end 1042 of the resecting component 1025 in its range of movement.

Figure 13:
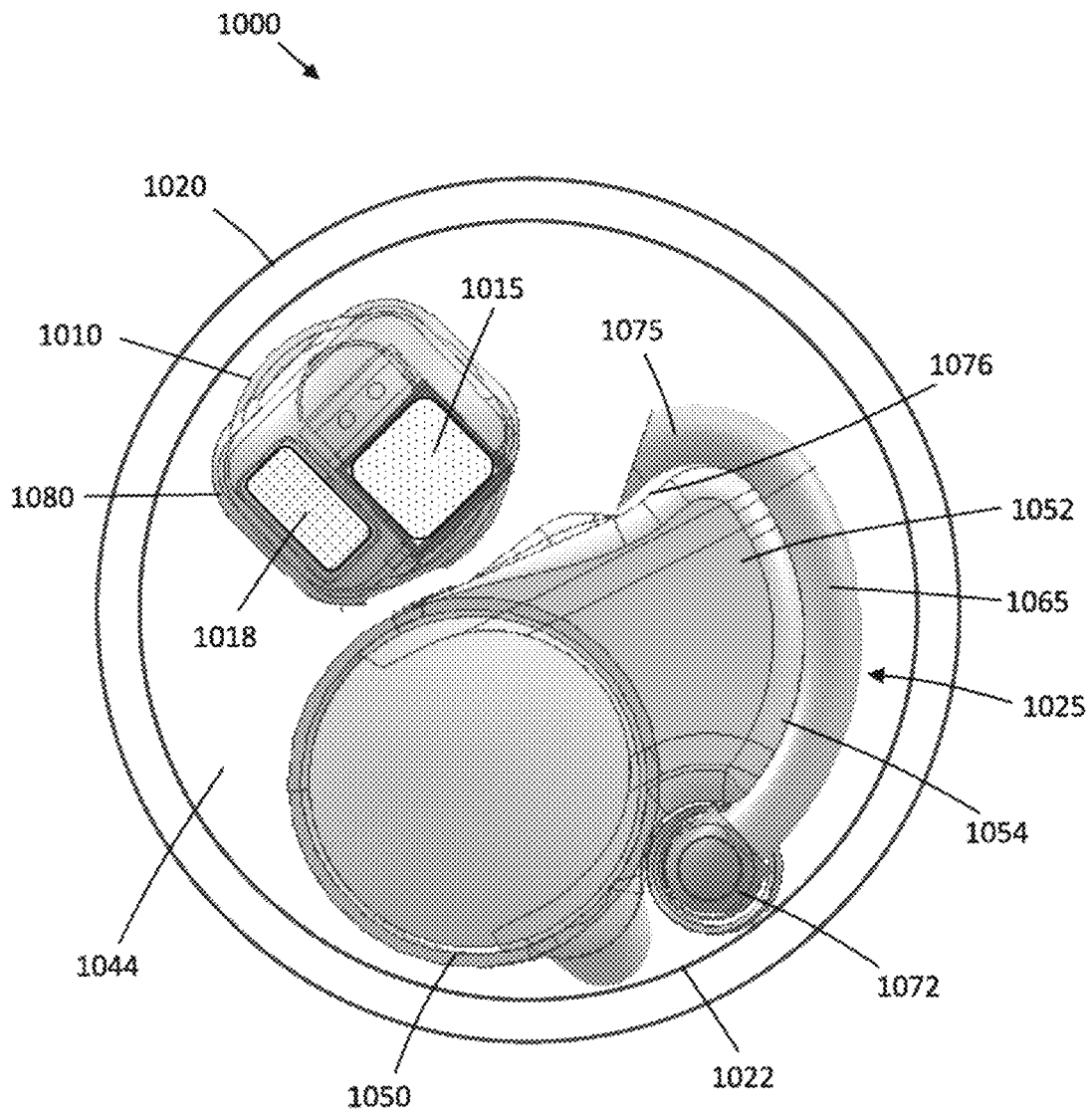
FIG. 13 is an end view of working end of the probe of FIGS. 11A-12.

Now turning to FIGS. 12 and 13, it can be seen how the sensor sleeve 1010 and the resecting component 1025 are housed within the interior passageway 1022 of the thin-wall outer sleeve 1020. The area or flow space 1044 within the outer sleeve 1020 not occupied by the resecting component 1025 and the sensor sleeve 1010 again comprises a fluid inflow channel as described previously.

Figure 14:
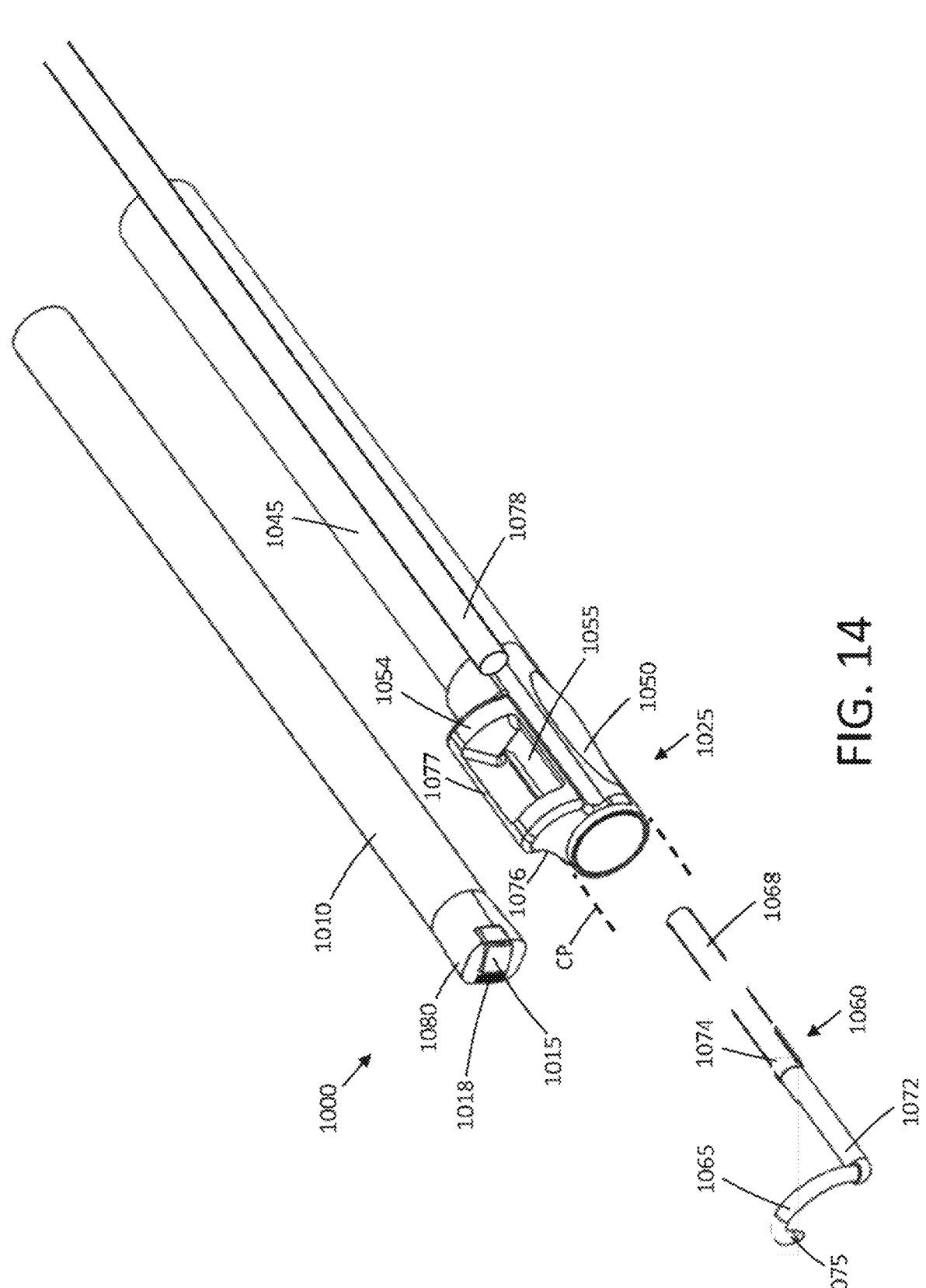
FIG. 14 is an exploded view of working end of FIGS. 11A-12 which shows the sensor sleeve and shaft of the resecting component.

FIG. 14 shows an exploded view of the resecting component 1025 and the imaging sleeve 1010 without the outer sleeve 1020. In the variation, it can be seen that the resecting component 1025 includes an elongated shaft 1045 with an interior tissue extraction channel 1048 therein. The shaft 1045 is coupled to the dielectric housing 1050 with a projecting portion 1052 that projects outward from the cylindrical periphery CP of the shaft 1045. An axially-extending curved surface 1054 of the projecting portion 1052 carries the resecting window 1055 which thus has the curvature of surface 1054. An RF electrode 1060 is adapted to reciprocate axially across the resecting window 1055 as described previously. The projecting portion 1052 and its curved surface 1054 are spaced outwardly from the cylindrical periphery CP of the resecting component shaft 1045 to allow for better viewing with the image sensor 1015 as well as functioning as a projecting feature that be pressed into targeted tissue for resecting more deeply than would possible with the working end 615 as shown in FIGS. 7 and 8 above.

As can be seen in FIGS. 13 and 14, the electrode 1060 has an active electrode tip portion 1065 that has a curvature to match the curved surface 1054 around resecting window 1055. The electrode 1060 has an elongated shaft portion 1068 which is covered with an insulative layers 1072 and 1074, such as a suitable heat shrink material. The purpose of extending the insulative layers 1072 and 1074 as close to active electrode tip portion 1065 as possible is to reduce the exposed electrode surface area, which in turn provides for enhancing RF current energy density in saline to enable plasma ignition at lower power levels. In variation of the working end, the surface area of the exposed, active electrode tip 1065 is. less than 8.0 mm$^2$, less than 7.0 mm$^2$ or les than 6.0 mm$^2$. In such variations, the electrode tip 1065 comprises a tungsten wire with a diameter ranging between 0.25 mm to 0.80 mm. In one variation shown in FIG. 15, the electrode tip comprises a tungsten wire having a diameter of 0.508 mm and an exposed surface area of 7.435 mm$^2$ which is operatively connected to a 170 W to 200 W RF generator providing a cutting waveform as is known in the art.

Of further interest, referring to FIG. 13, the active distal tip 1065 of electrode 1060 is configured with a distalmost hook shape 1075 that is adapted to hook over a cooperating undercut 1076 in the dielectric housing 1050 adjacent at outward edge 1077 of the resecting window 1055 as the electrode tip 1065 is effectively locked onto the axially-extending curved surface 1054 of the dielectric housing 1050 as the electrode tip 1065 reciprocates. The electrode shaft 1068 reciprocates in tube 1078 which is coupled to shaft 1045. This hooked shape 1075 of the active electrode tip 1065 prevents the electrode from being lifted away from the curved surface 1054 around the resecting window 1055 to insure effective cutting of tissue as the electrode tip 1065 sweeps across proximal and distal edges of the window 1055.

Referring again to FIGS. 14-15, it can be seen that the sensor sleeve 1010 comprises a thin-wall metal material, as stainless steel, that has a distal portion 1080 that is formed into a partly rectangular shape to receive the image sensor 1015 and the LED 1018.

Figure 15:
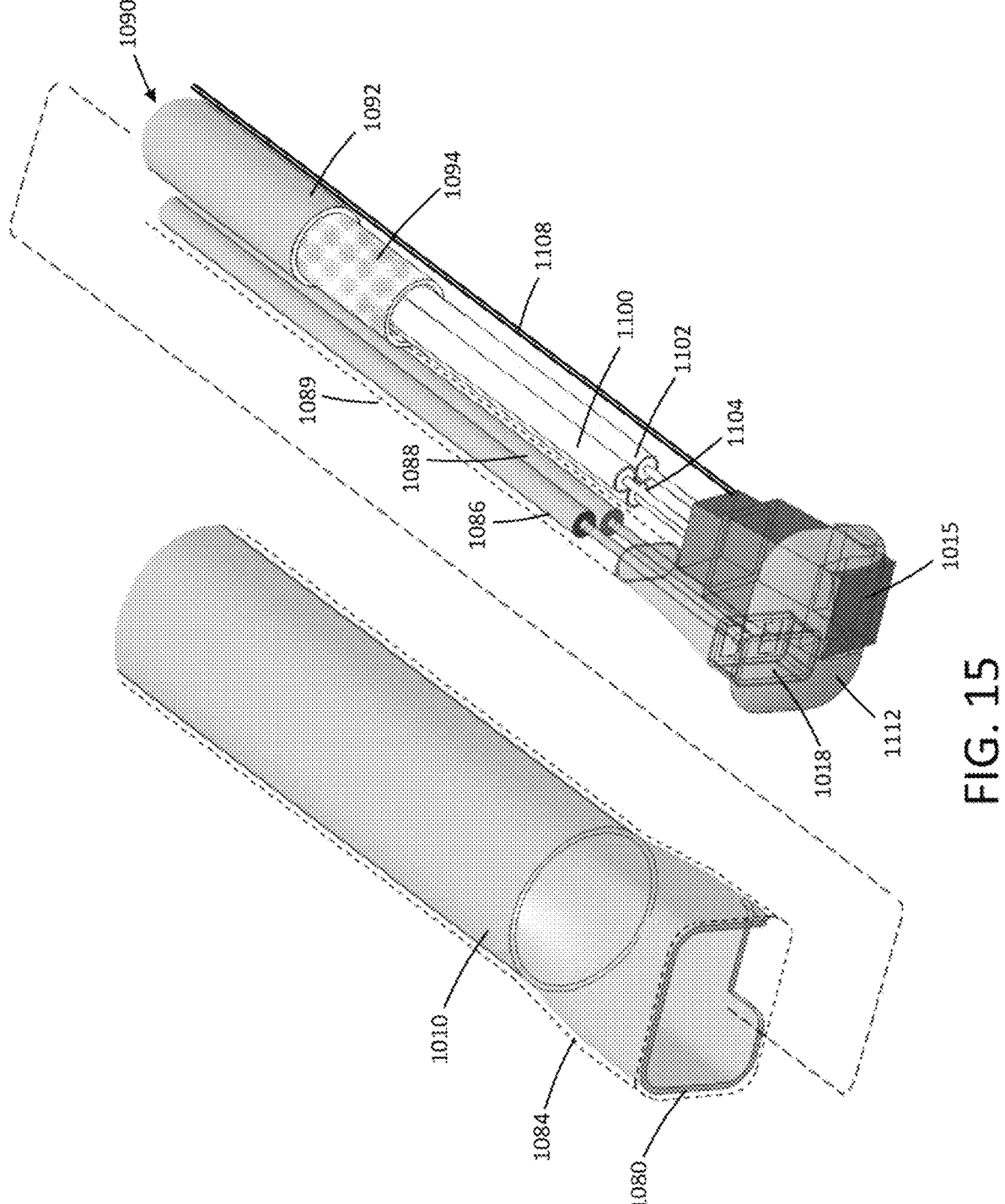
FIG. 15 is an enlarged view of the imaging component showing the sensor sleeve and sensor cable which illustrate the electromagnetic shielding aspects of the device.

As can be seen in FIG. 15, the sensor sleeve 1010 also is covered in a thin insulator layer 1084 which can be a heat shrink material (shown in broken line). The LED 1018 is connected to first and second electrical leads, 1086 and 1088 shown a partial cut-a-way view in FIG. 15, which powers the LED. The electrical leads 1086 and 1088 are additionally covered with an insulative layer 1089, such as a heat shrink material (shown in broken line).

Referring again to FIG. 15, the image sensor 1015 is connected to an image processor and power source by a sensor cable 1090 that includes an exterior jacket 1092 and electromagnetic shielding layer 1094 as is known in the art. The cable 1090 has a core that comprises as least one co-axial cable for carrying image signals from the sensor 1015. In one variation shown in FIG. 15, the sensor cable 1090 carries first, second and third co-axial cables 1100, 1102 and 1104. Each co-axial cable has a surface jacket over an electromagnetic shielding layer. Thus, the combination of the sensor sleeve 1010 and the sensor cable 1090 provide multiple layers of electromagnetic shielding which are adapted to prevent electrical interference from the electrode 1060 of the resecting component 1025 during use, or similar such interference from tools having motors, energy sources or the like. Such other tools can comprise mechanical cutting tools, laser tools, ultrasound tools, microwave tools, cryogenic tools and pressure sensing devices.

In a variation, the first co-axial cable 1100 is configured with conductors to carry image signals from the image sensor 1015 to the image processor in the handle or in a remote console. The second co-axial cable 1104 has at least one conductor which can at least one of a clock signal, a timing signal or an additional video signal. The third co-axial cable 1102 is configured with at least one conductor, and in a variation carries has a power conductor and a ground conductor. In some variations, another cable or electrical lead 1108 (see FIG. 15) can be provide which is used as a ground which may be at an exterior of the sensor cable 1090. Still referring to FIG. 15, the image sensor 1015 and the LED 1018 are fixed in place in the rectangular end 1080 of the sensor sleeve 1010 by a transparent bonding and setting material indicated at 1112, such as a suitable variation of Loctite.

Figure 16:
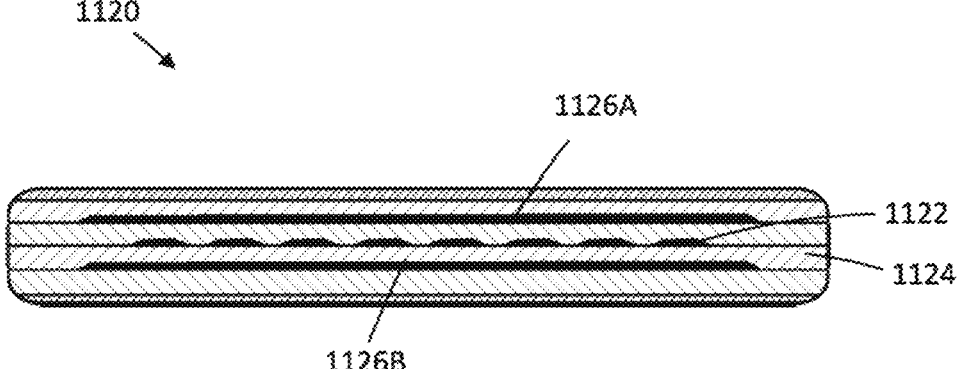
FIG. 16 is cross sectional view of a flex circuit that is configured for use as a shielded sensor cable.

In another variation similar to that of FIG. 15, the sensor cable 1010 may replaced by a flex circuit 1120 as shown in FIG. 16. Such a flex circuit 1120 is carried in an interior of the sensor sleeve 1010 of FIG. 15 and connected to the image sensor 1025 for carrying at least one of video signals, clock signals and timing signals. In such a flex circuit 1020 (FIG. 16), the conductors 1022 carrying such video, clock and timing signals are disposed in an interior layer 1024 of the flex circuit 1020. The flex circuit 1020 further comprises first and second metal shielding layers 1026A and 1026B on first and second sides of said interior layer 1024, where such first and second metal shielding layers 1026A, 1026B are configured to shield such video, clock and/or timing conductors 1022 from electrical interference from an RF source or other source of electrical interference. In such a flex circuit 1020, a ground conductor (not shown) can be disposed in the interior layer 1024 of the flex circuit or can be in a layer outside the metal shielding layers 1026A, 1026B. In one variation of such a flex circuit, one of the metal layers 1026A and 1026B can be is adapted to carry power to the image sensor.

Figure 17:
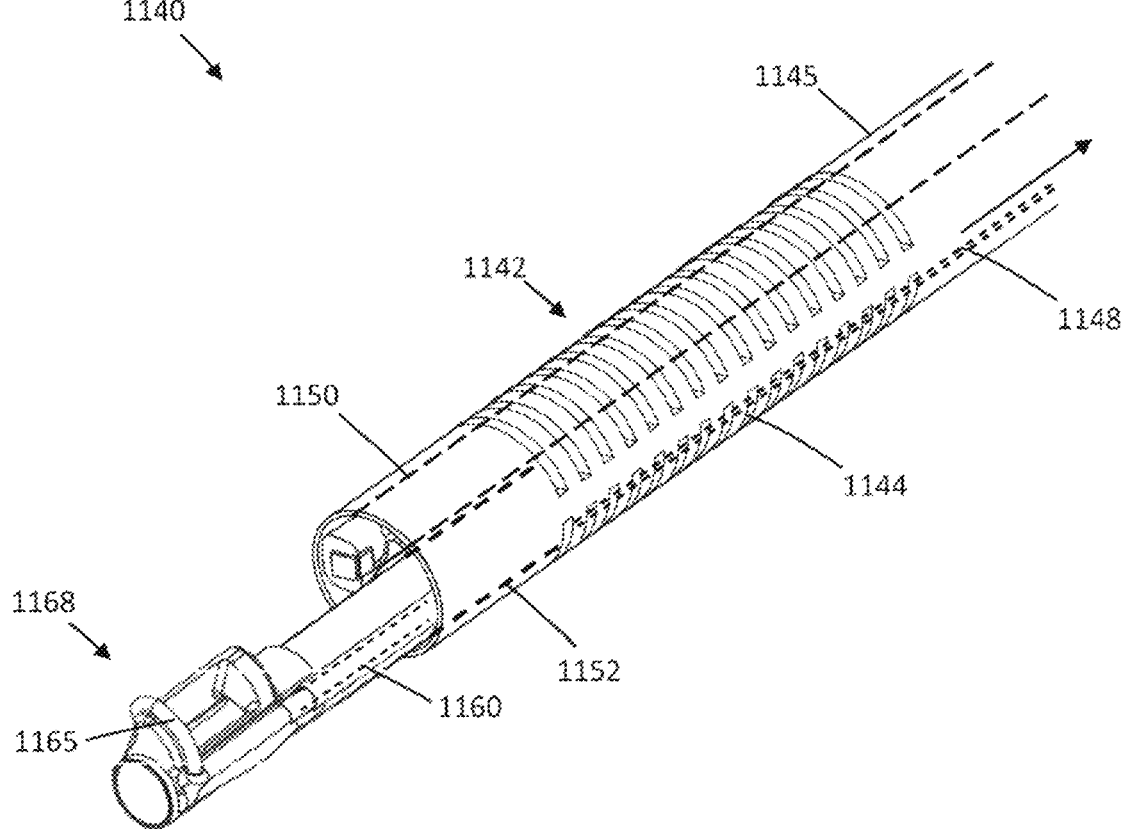
FIG. 17 is a perspective view of another variation of a working end similar to that of FIGS. 11A-15 provided with articulation functionality.

FIG. 17 illustrates another variation of working end 1140 of an imaging and resecting system that is similar to that of FIGS. 11A-15 except that the working end 1140 includes a shaft 1142 with an articulating region 1144. In this variation, the outer sleeve 1145 comprises a slotted tube with a pull wire 1148 (or co-axial slotted tube) that can articulate the outer sleeve as is known in the art. As can be easily understood, the sensor sleeve 1150 and shaft 1152 of the resecting component also are configured with flexible distal portions so as to flex as the outer sleeve 1145 is articulated. The sensor sleeve 1150 will still shield the interior sensor cable from electrical interference when provided with slots or perforations which allow it to bend. The flexible section of the shaft 1052 of the resecting component is elongated to allow the shaft to be extended and retracted during use. The electrode shaft 1160 also is flexible to allow reciprocation of the electrode 1165 in the working end 1168 of the resecting component.

Figure 18:
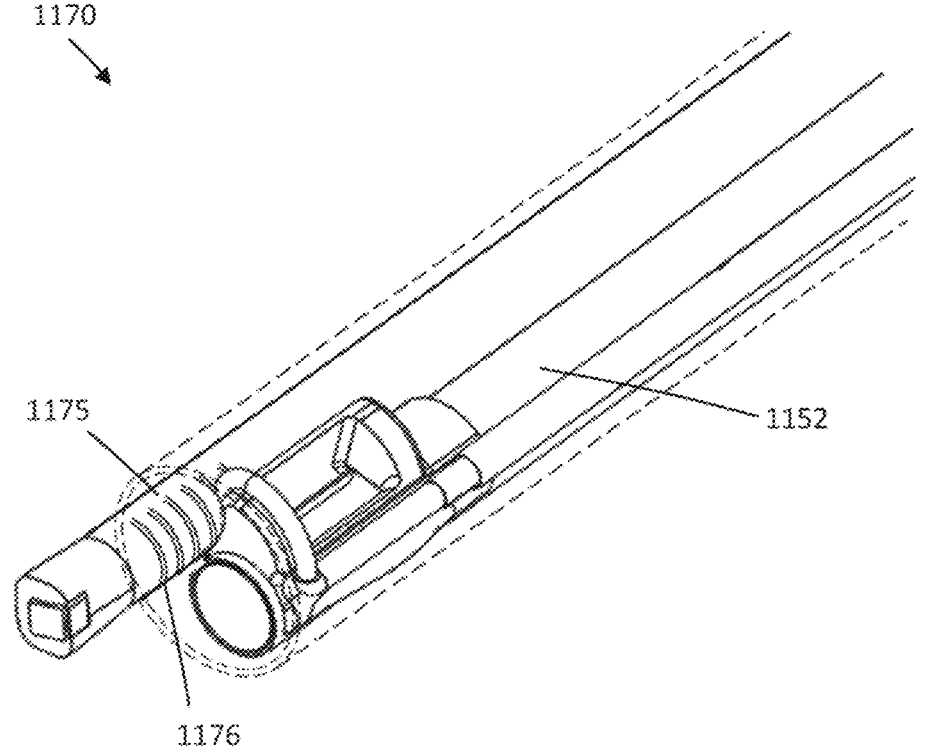
FIG. 18 is a perspective view of another variation of a working end with an articulating sensor sleeve.

FIG. 18 illustrates another variation of a working end 1170 which the sensor sleeve 1175 includes a slotted region 1176 for articulation with a pull-wire or co-axial slotted tube (not shown). In this variation, the sensor sleeve 1175 can be optionally extended and articulated to alter the viewing angle which may be useful in certain treatments, for example to view bladder tumors. Thus, the sensor shaft 1175 can be configured for extension and rotation, while at the same time the resecting component shaft can be configured for extension from the outer sleeve 1145.

Figure 19:
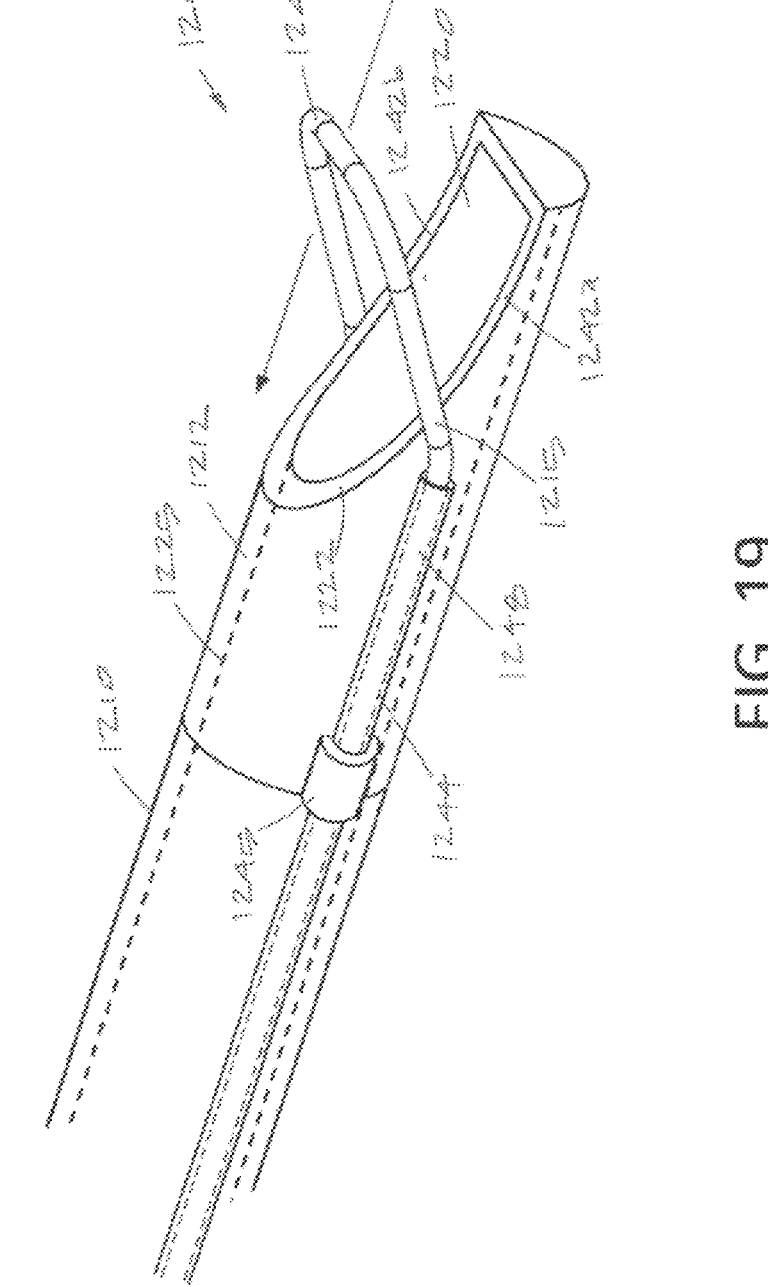
FIG. 19 is a perspective view of another variation of a resecting component and working end with different dielectric member and active electrode.
Figure 20:
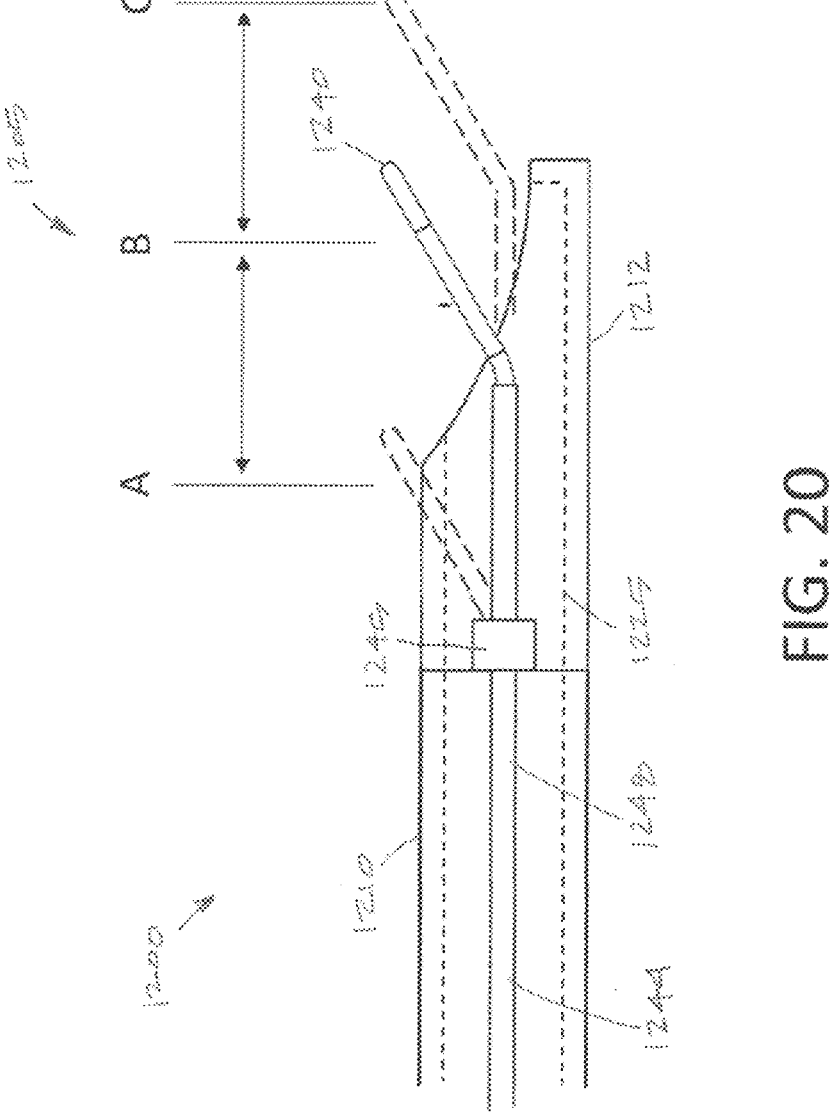
FIG. 20 is an elevational view of the working end of FIG. 19 illustrating various positions of the active electrode.

Now turning to FIGS. 19 and 20, another variation of resecting component or device 1200 with working end 1205 is shown that differs from previous variations. The resecting component 1200 again has an elongated extendable shaft 1210 with a distal dielectric housing 1212 and a reciprocating electrode member 1215. In this variation, the dielectric housing 1212 has a window 1220 configured as a scooped out region of a wall 1222 of the housing 1212. A negative pressure source again communicates with interior passageway 1225 in the shaft 1210 and dielectric housing 1212 to aspirated fluid and resected tissue chips away from a working space.

In this variation, the electrode member 1215 as a distal active electrode tip portion 1040 has a U-shaped curvature with a radius that allows the electrode tip to move proximally over the outside diameter of the shaft 1210. The active electrode tip portion 1040 is shown in exemplary extended and retracted positions A, B, and C in elevational and phantom views in FIG. 20. As can be seen in FIGS. 19 and 20, the active electrode tip 1040 is spaced apart from the edges 1242a and 1242b of window 1220. The electrode member 1215 has elongated shaft portions 1244 disposed on either side of shaft 1210 which extend through guides 1245 to the handle of the device, and are configured to be moved or reciprocated by the motor drive. The electrode shaft portions 1244 are covered with an insulative layer 1248 such as a suitable heat shrink material. The insulative layers 1248 extend as close to the active electrode tip portion 1040 as possible is to reduce the exposed active electrode surface area, as described above, to enhance RF current energy density about the tip portion 1240. As in previous variations, the surface area of the exposed, active electrode tip 1240 is less than 8.0 mm², less than 7.0 mm² or less than 6.0 mm². In such variations, the electrode tip 1240 comprises a tungsten wire with a diameter ranging between 0.25 mm to 0.80 mm.

In use, the resecting component 1200 and working 1205 are suited for bladder tumor resection procedures as described in co-pending, commonly owned and published US Patent Application 2021/0059748 titled SURGICAL DEVICE AND METHODS, which is incorporated herein by this reference. In the variation shown in FIGS. 19 and 20, the controller is configured with setting that allow for selection of various operating modes. In one variation, an operating mode is configured for continuous resection and the electrode tip 1040 is reciprocated at one or more selected reciprocation rates over a stroke that extends from position A to position C in FIG. 20 or where the stroke extends from position B to position C in FIG. 20. In another mode, the controller reciprocates the electrode tip 1040 in a single stroke to cut a single tissue chip. In these motor driven modes, the negative pressure source is activated to aspirated tissue and fluid chip into the window 1220.

In another variation, the controller can be used to move the electrode tip 1040 to a selected position, such as position B or position C in FIG. 20, and the stop movement of the electrode 1040 is such a fixed position. With the active electrode tip 1040 in such a fixed location, the physician then can manually move the electrode tip 104 over target issue to cut thin slices of tissue. In this mode, the negative pressure source would be activated simultaneously to remove the resected tissue. In all of the above modes, the active electrode tip 1040 is adapted to ablate though tissue without the scissor edge effect of the previous embodiments where the electrode sheared tissue across a window edge. In any of the variations of use just described, the controller can also use the active electrode 1040 for coagulation instead of cutting or ablation.

Figure 21:
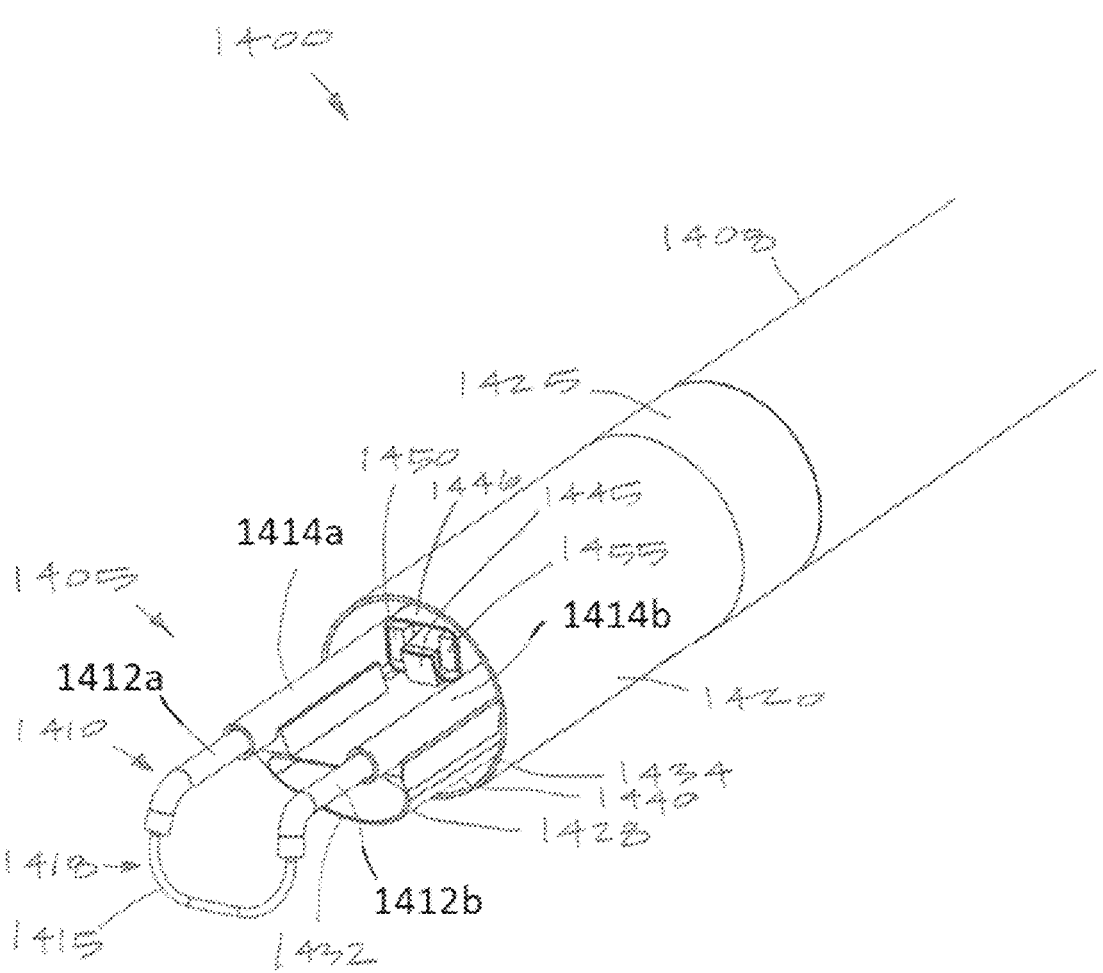
FIG. 21 is a perspective view of another variation of a working end of a resecting device that carries a reciprocating electrode, an extendable and retractable aspiration sleeve, an image sensor and at least two LEDs that emit light at different wavelengths for illuminating targeted tissue.
Figure 22:
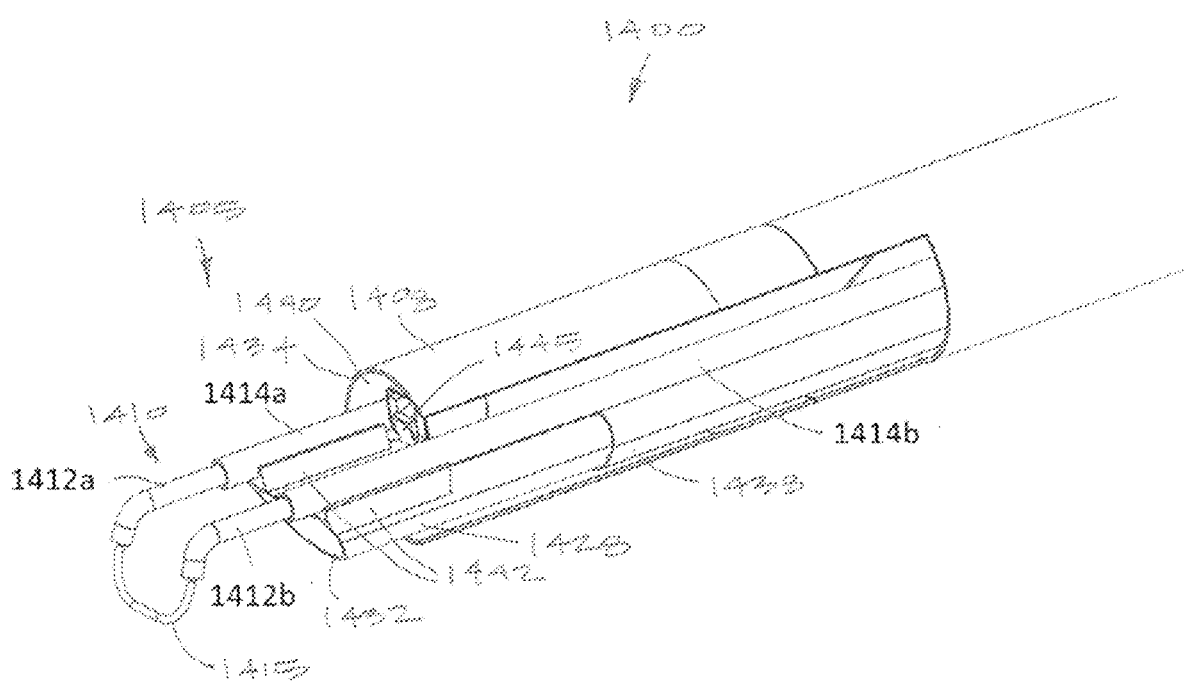
FIG. 22 is a partially cut-away view of the distal end of FIG. 21.

FIGS. 21 and 22 illustrate another variation of a resecting device 1400 with a working end 1405 carrying bi-polar electrode arrangement at the distal end of elongate outer sleeve 1408. The device 1400 is particularly adapted for resection of bladder tumors. In this variation, the working end 1405 is configured with a reciprocating loop electrode assembly 1410 that has first and second legs 1412a and 1412b that extend through respective guide sleeves 1414a and 1414b. The first and second legs 1412a and 1412b carry an insulative coating such as a heat shrink polymer. The guide sleeves 1414a and 1414b are typically a tube made from conductive material and act as the bi-polar return electrode or a tube made from non-conductive material while incorporating separate bi-polar return electrode. The active electrode 1415 comprises a tungsten wire or other suitable wire material that is exposed only around the distal tip 1418 of the loop electrode assembly 1410. The first and second legs 1412a, 1412b extend through the sleeve 1408 to the handle (not shown) and a manually operated actuator is adapted for axially reciprocation (axial back-and-forth movement) of the loop electrode assembly 1410. However, it should be appreciated that motorized reciprocation of the loop electrode 1410 is also possible. In FIGS. 21 and 22, the elongated sleeve 1408 may be a conductive metal that is covered with an insulator layer 1420 where the return electrode 1425 comprises one exposed section of the exterior surface of the sleeve 1408.

Referring again to FIGS. 21 and 22, the elongated sleeve 1408 also carries an aspiration channel 1428 with a distal end 1432 that is extendable and retractable relative to the distal end 1434 of the outer sleeve 1408. The aspiration channel 1428 may also be stationary. In the partial cut-away view of FIG. 22, it can be seen that the extendable and retractable aspiration channel 1428 slides with an outer aspiration sleeve 1438 that is recessed within the lumen 1440 of the elongate outer sleeve 1408. A remote negative pressure source communicates with the aspiration channel 1428. The aspiration channel 1428 is configured with guide elements or fins 1442 that extend upwardly on either side of the first and second legs 1412a and 1412b to maintain the alignment of the aspiration channel 1428 with the loop electrode assembly 1410 during extension and retraction of the aspiration channel. In one variation, the aspiration channel 1428 is adapted to reciprocate in unison with the loop electrode assembly 1410. In another variation, a manual actuator is provided in the handle (not shown) to extend and retract the aspiration channel 1428 while another actuator in the handle, or a motor, is adapted to reciprocate the loop electrode assembly 1410. In a variation, at least a distal portion of the aspiration channel 1428 is fabricated of a transparent material to allow a light from a light source to pass through the walls or the aspiration channel 1428 to illuminate the tissue targeted for resection.

Referring again to FIG. 21, the working 1405 carries an image sensor 1445 carried at the distal end of sensor sleeve 1446 as described in previous variations. The sensor sleeve 1446 is highly insulated to prevent electromagnetic interference with the electrical leads extending from the image sensor 1445 to the handle of the device 1400. As described above, the activation of the bi-polar electrode arrangement can potentially cause interference with the image sensor. As also can be seen in FIG. 21, the distal end of sensor sleeve 1446 carries first and second LEDs 1450 and 1455 adjacent to the image sensor 1440. In one variation, the first LED 1450 provides a typical white light with wavelengths suited for illuminating a working space as is known in the art.

In this variation, the second LED 1455 emits a blue light wavelength or wavelengths that are adapted for use in resecting bladder tumors. Bladder cancer can be confirmed during an outpatient surgery which is called transurethral resection of a bladder tumor (TURBT). As is known in the art, blue light cystoscopy is used to assist in such a TURBT procedure. In advance of such a cystoscopy, the physician introduces a catheter through the urethra into the bladder and injects an imaging agent (e.g., Cysview) into the bladder for a period of time, for example, 30 to 60 minutes. The bladder cancer cells multiply more rapidly than the surrounding normal bladder lining, and such cancerous cells can preferentially absorb the imaging agent. When blue light is used to illuminate the bladder wall, the cancer cells glow in a shade of fluorescent pink, which then allows the physician to more accurately resect the tumor and margins around the tumor. Thus, the second LED 1455 that emits blue light can assist in the tumor resection. The handle can include a switch mechanism for toggling between white light, blue light or both at the same time. Alternatively, a mechanism can be provided to automatically activate the blue light LED 1455 in a sequence together with the white light LED 1450. In general, an imaging and resecting device of the invention comprises a handle coupled to an elongated shaft extending about a longitudinal axis to a working end, a moveable electrode carried at the working end, a motor configured to move the electrode to resect tissue, an image sensor carried at the working end with field of view adapted for viewing the moveable electrode while cutting tissue, a first LED carried at the working end having wavelength of a white light for illuminating a working space and a second LED carried at the working end having blue light wavelengths for identifying cancerous tissue.

Figure 23:
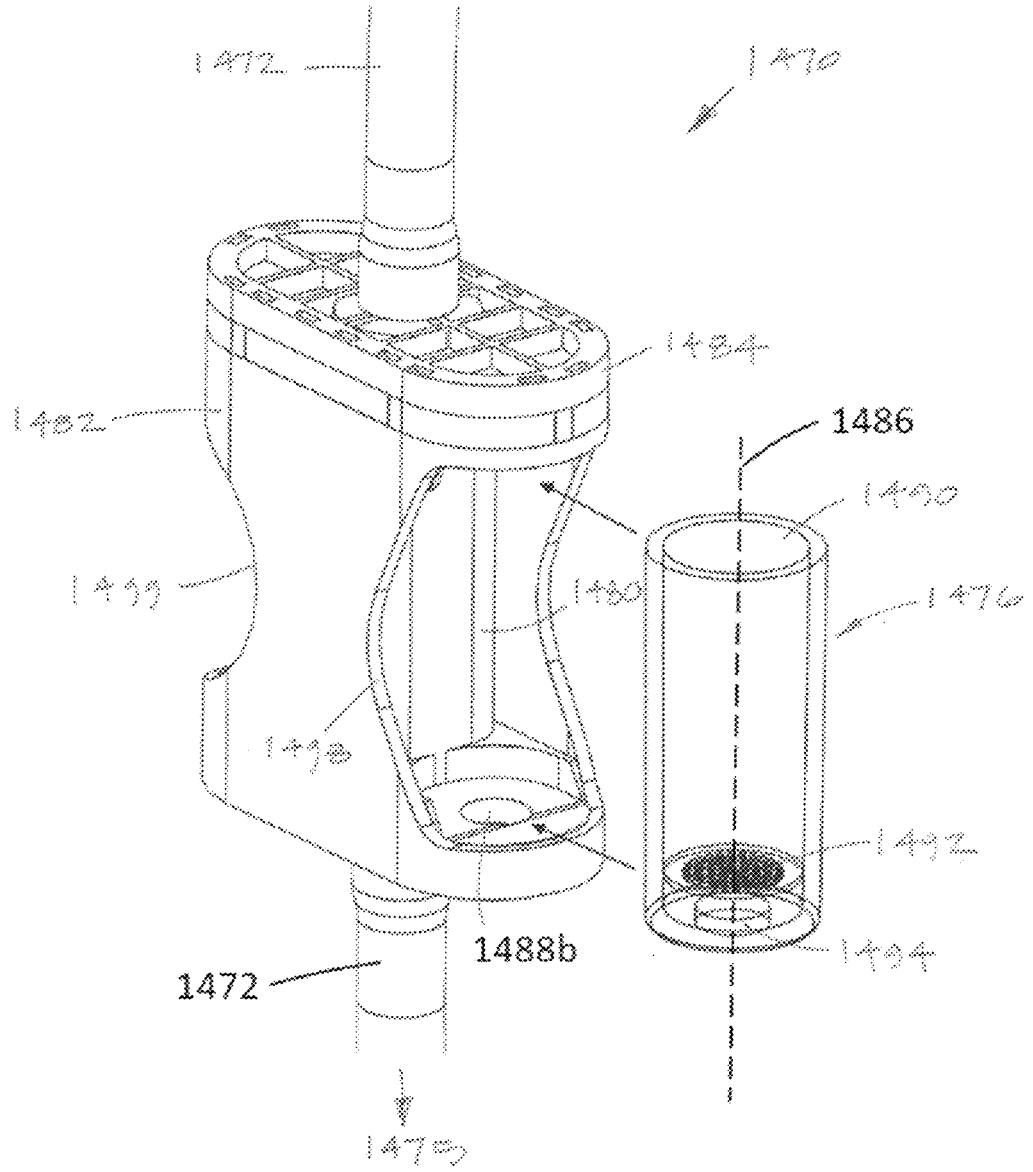
FIG. 23 is a tissue trap of the invention that allows for insertion and removal of the tissue collection chamber during use.
Figure 24:
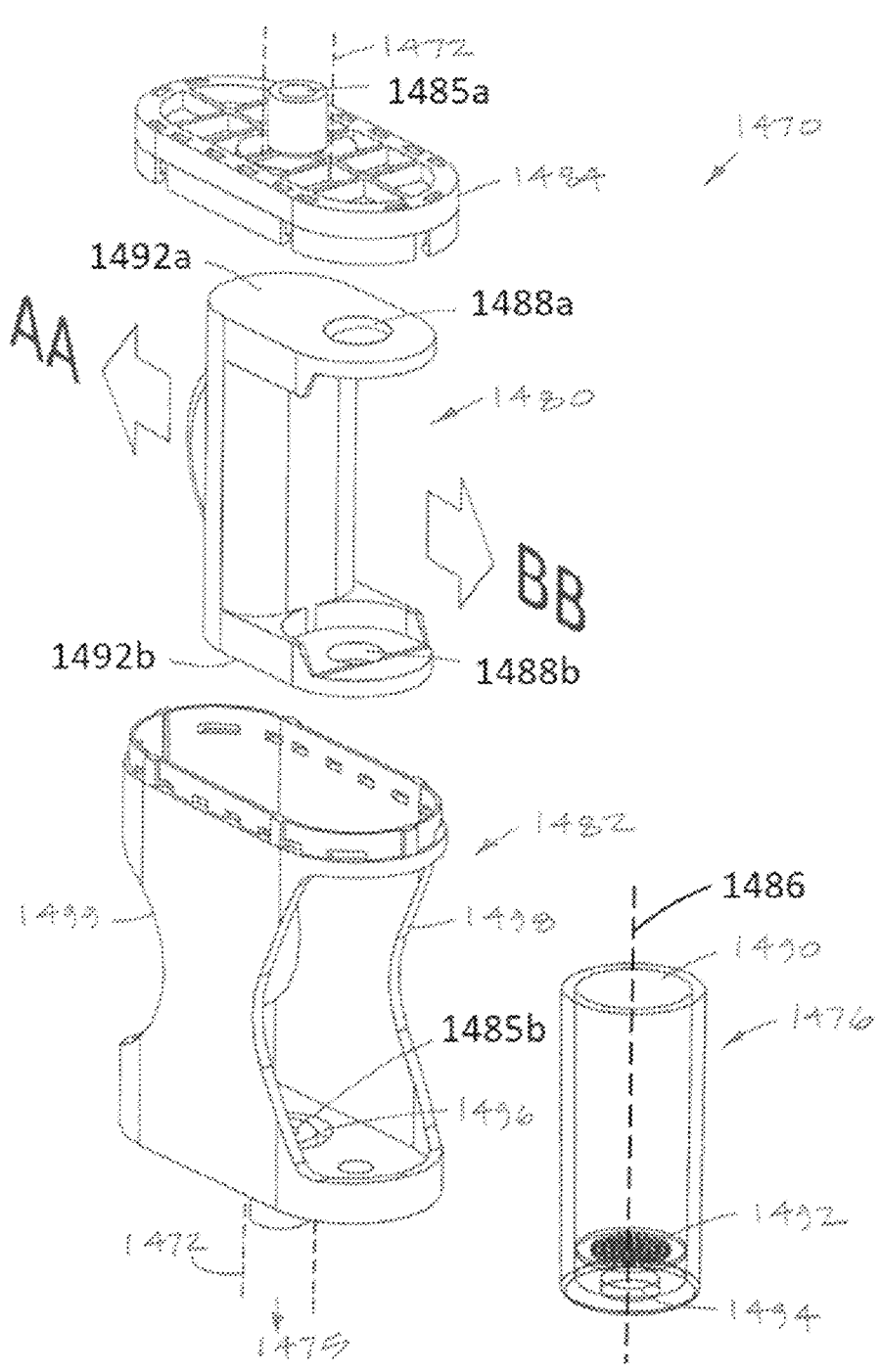
FIG. 24 is an exploded view of the parts of the tissue trap of FIG. 23.

Now turning to FIGS. 23 and 24, the resecting devices of the present invention may be combined or configured with a tissue trap or tissue collector 1470 which may be positioned in fluid outflow tubing 1472 that extends from an outflow port 1485B at the bottom of the tissue removal or resection device. The fluid outflow tubing 1472 is configured to discharge fluid waste in the direction of arrow 1475 to a waste fluid collection reservoir (not shown) in a manner similar to that previously described with respect to fluid outflow tubing 712. As described above, a negative pressure source communicates with the aspiration channel 1428 (FIG. 21) though the outflow or aspiration tubing 1472 of FIG. 23. The purpose of the tissue trap or collector 1470 is to capture resected tissue fragments, often referred to as "chips," which then can be analyzed for malignancies and other tissue abnormalities.

The tissue trap 1470 includes a removable tissue collection vial or chamber 1476 that can be removed and exchanged rapidly during a procedure, which is very useful and allows for immediate evaluation of captured tissue chips, even while the procedure continues. The collection vial or chamber 1476 is preferably at least partially transparent and can be inserted into a slidable receiving tray 1480, best seen in FIG. 24. The receiving tray 1480 is configured to slide laterally in the trap or collector housing 1482, and a housing cap 1484 aligns a trap inflow port 1485*a* and trap outflow port 1485*b* with a centerline 1486 of the collection vial or chamber 1476.

FIG. 24 is an exploded view of the tissue trap 1475 showing the sliding tray which is 1480 is adapted to slide laterally back- and forth in the directions of arrows AA and BB within an interior of the housing 1482. The housing cap 1484 is designed to be removed to allow insertion and removal of the sliding tray 1480 in the housing 1482.

When the sliding tray 1480 is positioned fully in the direction of arrow AA, the trap inflow port 1485*a* is aligned with upper tray opening 1488*a* and the lower tray opening 1488*b* is aligned with the trap outflow port 1485*b*. As can be understood, the transparent collection chamber 1476 has an upper open end 1490 and a mesh filter 1492 in a lower open end 1494. When the sliding tray is in positioned fully in the direction of arrow BB, the superior surface 1492*a* of the sliding tray 1480 seals the trap inflow port 1485*a* with an O-ring or other suitable flexible seal (not visible), and the inferior surface 1492*b* of the tray 1480 seals the trap outflow port 1485*b* which has an O-ring or other flexible seal in a groove 1496 which circumscribes the port 1485*b*. Thus, when the sliding tray 1480 is pushed fully in the direction of arrow BB, the inflow and outflow ports 1485*a* and 1485*b* are sealed and the collection chamber 1476 can be removed from the sliding tray 1480 and replaced. The sliding tray 1480 and collection chamber 1476 can be pushed laterally by manual manipulation, where the openings 1498 and 1499 in opposing sides or the housing 1482 allows the physician or nurse to push the sliding tray 1480 and collection chamber 1476 from side to side in the directions of arrows AA and BB, respectively (FIG. 24).

During use, the collection vial 1476 may be removed from the collector housing 1482 through the opening 1498 in the collection housing 1482 after the sliding tray 1480 has been pushed fully in the direction of arrow BB to block inflow from the fluid outflow tubing 1472. Additionally, of course, the fluid management pump(s) will also be shut off to stop most fluid circulation. A new collection vial 1476 may be reintroduced through the opening 1498 and the sliding tray pushed in the direction od arrow AA to align the collection vial with the fluid outflow tubing 1472, allowing fluid flow to be restarted and tissue resection to be resumed. While generally not preferred, in some instances the entire collection housing 1482 may be removed from the fluid outflow tubing 1472 and replaced with a new collection housing.

In another embodiment, the flow management system may be programmed to enhance fluid and tissue aspiration from reciprocating cutter resection devices. Resection devices coupled to conventional fluid management systems with low and/or constant inflow (perfusion) and outflow (aspiration) flow rate can have difficulty in collecting and removing tissue material in the outflow stream That can be disadvantageous in TURBT and other applications where rapid and efficient tissue evacuation and collection may be required for biopsy purposes.

To enhance tissue and fluid collection, the fluid management systems of the present invention can be constructed to alter the inflow perfusion and outflow flow aspiration rates from, for example, inflow tubing 710 and outflow tubing 712 in control console 145, as shown in FIGS. 1 and 2. The reciprocating cutter resection devices may be provided with sensors or other features configured to detect the location of the resecting head or the electrode relative to the tool sheath. The system controller 145 will be coupled to the sensors and programmed to identify the location of the resecting head or the electrode as it is reciprocated. When the resecting head is not in operation, the fluid inflow and outflow are held generally constant and at a low level to maintain the pressure in the bladder or other cavity. Typically, when resection starts, the resecting tip or electrode extends distally from the sheath. The user then energizes the electrode and engages the resecting head or loop against the tissue and retracts the tip or electrode over the tissue to effect the desired tissue resection.

During the resection stroke, the controller in console 145 increases the outflow through the outflow tubing 712 to evacuate the fluid including tissue and blood. To maintain pressure in the bladder or other body cavity, the controller will adjust the inflow pump speed based on a difference between a measured pressure in the cavity and a set pressure. At the end of the resection stroke, the resecting tip or the electrode is partially or fully retracted back into the sheath, and the user deenergizes the electrode to end resection. The controller may detect de-energization and/or a retracted position of the electrode and adjust the inflow and outflow rates to optimize the tissue evacuation capability. In one example, the controller can further increase the outflow rate while decreasing the inflow rate, typically for a set period of few seconds, to increase the suction through the outflow channel while limiting the "push" from the irrigation fluid from the inflow channel After that set amount of time, when the controller determines that the device is no longer at the end of a resection stroke, the inflow and outflow pump speed can return to the resting state flow rate.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A tissue trap for use with a tissue removal device having a fluid outflow connector configured to direct waste fluid to a waste fluid collection reservoir, said tissue trap comprising:

a collector housing having (a) a fluid inflow port configured to receive waste fluid from the fluid outflow connector of the tissue removal device and (b) a fluid outflow port configured to direct filtered waste fluid to the fluid collection reservoir;

a collector vial having an inlet end, and outlet end, and a filter member therebetween; and a carrier disposed in an interior of the collector housing, said carrier configured to (a) removably carry the collector vial and (b) move between (i) a first position where the inlet and outlet ends of the collector vial are aligned with the fluid inflow and outflow ports of the collector housing to allow fluid flow, filtration, and collection and (ii) a second position where at least the fluid inflow port of the collector housing is sealed to block fluid flow from the fluid outflow connector.

2. The tissue trap of claim 1, wherein the collector housing has at least one lateral opening configured to allow placement of the collector vial on the carrier and removal of the collector vial from the carrier.

3. The tissue trap of claim 2, wherein the collector housing comprises a positioning tray having a superior bracket and an inferior bracket, wherein the lateral opening is disposed between the superior bracket and the inferior bracket.

4. The tissue trap of claim 3, wherein (a) the superior bracket has an inflow opening which seals to the inlet end of the collector vial when the collector vial is mounted on the tray and (b) the inferior bracket has an outflow opening which seals to the outlet end of the collector vial when the collector vial is mounted on the tray.

5. The tissue trap of claim 4, wherein the tray in the first position (a) aligns the inflow opening in the superior bracket with the inflow port of the housing to allow fluid flow into the collection vial and (b) aligns the outflow opening in the inferior bracket with the outflow port of housing to allow fluid outflow from the vial to the waste fluid collection reservoir.

6. The tissue trap collector of claim 4, wherein the tray in the second position aligns the inflow opening in the superior bracket with a first solid surface of the collector housing to block fluid flow into the collection vial.

7. The tissue trap collector of claim 6, wherein the tray in the second position aligns the outflow opening in the inferior bracket with a second solid surface of the collector housing to block fluid flow out of the collection vial.

8. The tissue trap of claim 1, wherein the collector vial comprises a transparent material.

9. The tissue trap of claim 1, wherein collector vial is exposed on opposing sides of the housing and configured for manual manipulation between the first position and the second position in the housing.

10. A tissue removal system, comprising:

a tissue removal device having a fluid outflow connector configured to direct waste fluid to a waste fluid collection reservoir; and the tissue trap of claim 1.

11. The tissue removal system of claim 10, further comprising a fluid management system for circulating fluid flow from a fluid source through the tissue removal device and fluid outflow connector to the waste fluid collection reservoir.

* * * * *